US010351560B2

(12) United States Patent
Aissaoui et al.

(10) Patent No.: US 10,351,560 B2
(45) Date of Patent: Jul. 16, 2019

(54) CRYSTALLINE FORMS

(71) Applicant: IDORSIA PHARMACEUTICALS LTD, Allschwil (CH)

(72) Inventors: Hamed Aissaoui, Allschwil (CH); Christoph Boss, Allschwil (CH); Patrick Bouis, Allschwil (CH); Julien Hazemann, Allschwil (CH); Romain Siegrist, Allschwil (CH); Markus Von Raumer, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 15/759,710

(22) PCT Filed: Sep. 14, 2016

(86) PCT No.: PCT/EP2016/071637
§ 371 (c)(1),
(2) Date: Mar. 13, 2018

(87) PCT Pub. No.: WO2017/046125
PCT Pub. Date: Mar. 23, 2017

(65) Prior Publication Data
US 2019/0047996 A1 Feb. 14, 2019

(30) Foreign Application Priority Data

Sep. 15, 2015 (WO) ................. PCT/EP2015/071060

(51) Int. Cl.
*C07D 471/04* (2006.01)
*A61P 37/02* (2006.01)
*A61P 37/08* (2006.01)

(52) U.S. Cl.
CPC ............ *C07D 471/04* (2013.01); *A61P 37/02* (2018.01); *A61P 37/08* (2018.01); *C07B 2200/13* (2013.01)

(58) Field of Classification Search
CPC ......... C07D 471/04; A61P 37/02; A61P 37/08
USPC ...................................................... 514/275
See application file for complete search history.

(56) References Cited

U.S. PATENT DOCUMENTS

| 4,808,608 | A | 2/1989 | Guindon et al. |
| 4,965,258 | A | 10/1990 | Boshagen et al. |
| 7,534,897 | B2 | 5/2009 | Tanimoto et al. |
| 7,714,132 | B2 | 5/2010 | Fecher et al. |
| 7,897,788 | B2 | 3/2011 | Fecher et al. |
| 8,039,474 | B2 | 10/2011 | Fecher et al. |
| 8,143,304 | B2 | 3/2012 | Fretz et al. |
| 8,697,869 | B2 | 4/2014 | Aissaoui et al. |
| 9,096,595 | B2 | 8/2015 | Aissaoui et al. |
| 9,850,241 | B2 | 12/2017 | Aissaoui et al. |
| 9,879,006 | B2 | 1/2018 | Aissaoui et al. |
| 2005/0171143 | A1 | 8/2005 | Tanimoto et al. |
| 2007/0191416 | A1 | 8/2007 | Fecher et al. |
| 2007/0208004 | A1 | 9/2007 | Fecher et al. |
| 2009/0270414 | A1 | 10/2009 | Fecher et al. |
| 2010/0063103 | A1 | 3/2010 | Armer et al. |
| 2010/0190830 | A1 | 7/2010 | Fretz et al. |
| 2010/0234396 | A1 | 9/2010 | Fecher et al. |
| 2010/0234415 | A1 | 9/2010 | Berthelette et al. |
| 2011/0311483 | A1 | 12/2011 | Jia et al. |
| 2013/0065902 | A1 | 3/2013 | Aissaoui et al. |
| 2014/0045870 | A1 | 2/2014 | Aissaoui et al. |
| 2017/0022196 | A1 | 1/2017 | Aissaoui et al. |
| 2017/0129884 | A1 | 5/2017 | Aissaoui et al. |

FOREIGN PATENT DOCUMENTS

| CN | 103450218 A | 12/2013 |
| EP | 0242518 A1 | 10/1987 |
| EP | 0425906 A2 | 5/1991 |
| EP | 1505061 A1 | 2/2005 |
| EP | 1600440 A1 | 11/2005 |
| EP | 1852420 A1 | 11/2007 |
| EP | 1911759 A1 | 4/2008 |
| EP | 1916245 A1 | 4/2008 |
| EP | 1932839 A1 | 6/2008 |
| GB | 2388540 A | 11/2003 |
| GB | 2407318 A | 4/2005 |
| GB | 2422829 A | 8/2006 |
| GB | 2422830 A | 8/2006 |
| GB | 2422831 A | 8/2006 |
| WO | WO 01/78697 A2 | 10/2001 |
| WO | WO 01/79169 A2 | 10/2001 |
| WO | WO 02/094830 A2 | 11/2002 |
| WO | WO 03/051837 A2 | 6/2003 |

(Continued)

OTHER PUBLICATIONS

Arimura et al., "Prevention of Allergic Inflammation by a Novel Prostaglandin Receptor Antagonist, S-5751," The Journal of Pharmacology and Experimental Therapeutics, vol. 298, 2001, pp. 411-419.

Birkinshaw et al., "Discovery of potent CRTh2 (DP2) receptor antagonists," Bioorg. Med. Chem Let. 2006, vol. 16, pp. 4287-4290.

European Pharmacopeia Technical Guide, 5.11. Characters Section in Monographs, 1999, p. 695.

Fretz et al., J. Med. Chem. 2013, vol. 56, pp. 4899-4911.

Gallant et al., "Discovery of MK-7246, a selective CRTH2 antagonist for the treatment of respiratory diseases," Bioorganic & Med. Chem. Letters, 2011, vol. 21(1), pp. 288-293.

Géhin et al., "A Novel CRTH2 Antagonist: Single- and Multiple-Dose Tolerability, Pharmacokinetics, and Pharmacodynamics of ACT-453859 in Healthy Subjects," J. Clin. Pharmacol. 2015, vol. 55(7), pp. 787-797.

Griesser et al., "The Importance of Solvates," Polymorphism in the Pharmaceutical Industry (Ed. R. Hilfiker, VCH, 2006), Chapter 8, pp. 211-233.

(Continued)

Primary Examiner — Yong L Chu
(74) Attorney, Agent, or Firm — Arent Fox LLP

(57) ABSTRACT

The invention relates to a crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid, processes for the preparation thereof, pharmaceutical compositions comprising said crystalline forms, pharmaceutical compositions prepared from such crystalline forms, and their use as a medicament, especially as $CRTH_2$ receptor modulators.

13 Claims, 6 Drawing Sheets

(56) References Cited

FOREIGN PATENT DOCUMENTS

| | | |
|---|---|---|
| WO | WO 03/062200 A2 | 7/2003 |
| WO | WO 03/066046 A1 | 8/2003 |
| WO | WO 03/066047 A1 | 8/2003 |
| WO | WO 03/097042 A1 | 11/2003 |
| WO | WO 03/097598 A1 | 11/2003 |
| WO | WO 03/101961 A1 | 12/2003 |
| WO | WO 03/101981 A1 | 12/2003 |
| WO | WO 2004/007451 A1 | 1/2004 |
| WO | WO 2004/039807 A1 | 5/2004 |
| WO | WO 2004/078719 A1 | 9/2004 |
| WO | WO 2004/103970 A1 | 12/2004 |
| WO | WO 2004/106302 A1 | 12/2004 |
| WO | WO 2004/111047 A2 | 12/2004 |
| WO | WO 2005/019171 A1 | 3/2005 |
| WO | WO 2005/033099 A2 | 4/2005 |
| WO | WO 2005/040112 A1 | 5/2005 |
| WO | WO 2005/040114 A1 | 5/2005 |
| WO | WO 2005/044260 A1 | 5/2005 |
| WO | WO 2005/054232 A1 | 6/2005 |
| WO | WO 2005/056527 A1 | 6/2005 |
| WO | WO 2005/073234 A2 | 8/2005 |
| WO | WO 2005/094816 A1 | 10/2005 |
| WO | WO 2005/095397 A1 | 10/2005 |
| WO | WO 2005/121141 A1 | 12/2005 |
| WO | WO 2005/123731 A2 | 12/2005 |
| WO | WO 2006/034418 A2 | 3/2006 |
| WO | WO 2006/034419 A2 | 4/2006 |
| WO | WO 2006/036994 A2 | 4/2006 |
| WO | WO 2006/063763 A1 | 6/2006 |
| WO | WO 2006/070325 A2 | 7/2006 |
| WO | WO 2006/081343 A1 | 8/2006 |
| WO | WO 2006/090817 A1 | 8/2006 |
| WO | WO 2006/092579 A1 | 9/2006 |
| WO | WO 2006/095183 A1 | 9/2006 |
| WO | WO 2006/125784 A1 | 11/2006 |
| WO | WO 2006/136859 A2 | 12/2006 |
| WO | WO 2007/010964 A1 | 1/2007 |
| WO | WO 2007/010965 A1 | 1/2007 |
| WO | WO 2007/019675 A1 | 2/2007 |
| WO | WO 2007/022501 A2 | 2/2007 |
| WO | WO 2007/029629 A1 | 3/2007 |
| WO | WO 2007/031747 A1 | 3/2007 |
| WO | WO 2007/045867 A1 | 4/2007 |
| WO | WO 2007/065683 A1 | 6/2007 |
| WO | WO 2007/065684 A2 | 6/2007 |
| WO | WO 2007/065924 A1 | 6/2007 |
| WO | WO 2007/068418 A1 | 6/2007 |
| WO | WO 2007/107772 A1 | 9/2007 |
| WO | WO 2007/138282 A2 | 12/2007 |
| WO | WO 2007/144127 A1 | 12/2007 |
| WO | WO 2008/012511 A1 | 1/2008 |
| WO | WO 2008/014186 A1 | 1/2008 |
| WO | WO 2008/017989 A1 | 2/2008 |
| WO | WO 2008/074966 A1 | 6/2008 |
| WO | WO 2008/078069 A1 | 7/2008 |
| WO | WO 2008/113965 A1 | 9/2008 |
| WO | WO 2009/044134 A1 | 4/2009 |
| WO | WO 2009/044147 A1 | 4/2009 |
| WO | Wo 2009/049021 A1 | 4/2009 |
| WO | WO 2009/061676 A2 | 5/2009 |
| WO | WO 2009/063202 A2 | 5/2009 |
| WO | WO 2009/063215 A2 | 5/2009 |
| WO | WO 2009/077728 A1 | 6/2009 |
| WO | WO 2009/090399 A1 | 7/2009 |
| WO | WO 2009/090414 A1 | 7/2009 |
| WO | WO 2009/093026 A1 | 7/2009 |
| WO | WO 2009/093029 A1 | 7/2009 |
| WO | WO 2009/096526 A1 | 8/2009 |
| WO | WO 2009/140642 A2 | 11/2009 |
| WO | WO 2010/006939 A1 | 1/2010 |
| WO | WO 2010/006944 A1 | 1/2010 |
| WO | WO 2010/008864 A1 | 1/2010 |
| WO | WO 2010/031182 A1 | 3/2010 |
| WO | WO 2010/031183 A1 | 3/2010 |
| WO | WO 2010/031184 A1 | 3/2010 |
| WO | WO 2010/039982 A1 | 4/2010 |
| WO | WO 2010/054113 A2 | 5/2010 |
| WO | WO 2010/054114 A2 | 5/2010 |
| WO | WO 2010/085820 A2 | 7/2010 |
| WO | WO 2010/099039 A1 | 9/2010 |
| WO | WO 2010/142934 A1 | 12/2010 |
| WO | WO 2011/006936 A1 | 1/2011 |
| WO | WO 2011/055270 A1 | 5/2011 |
| WO | WO 2011/117798 A1 | 9/2011 |
| WO | WO-2011117798 A1 * 9/2011 ........... C07D 209/88 |
| WO | WO 2012/009134 A1 | 1/2012 |
| WO | WO 2012/009137 A1 | 1/2012 |
| WO | WO 2012/140612 A1 | 10/2012 |
| WO | WO 2015/140684 A1 | 9/2015 |
| WO | WO 2015/140701 A1 | 9/2015 |

OTHER PUBLICATIONS

Ha et al., "Synthesis of Tetrahydrocarbazole Derivatives as Potent-beta3-Adrenoceptor Agonists," Bull. Korean Chem. Soc., 2004, vol. 25(12), pp. 1784-1790.

Handbook of Pharmaceutical Salts. Properties, Selection and Use. , P. Heinrich Stahl, Camille G. Wermuth (Eds.), Wiley-VCH, 2008, (24 pages).

Ishizuka et al., "Ramatroban (BAY u 3405): A Novel Dual Antagonist of TXA2 Receptor and CRTh2, a Newly Identified Prostaglandin D2 Receptor," Cardiovascular Drug Rev. 2004, vol. 22(2), pp. 71-90.

Joo et al., "PGD Synthase and PGD2 in Immune Response," Mediators of Inflammation, vol. 2012, Article ID 503128; doi: 10.1155/2012/503128, pp. 1-6.

Luker et al., "Substituted indole-1-acetic acids as potent and selective CRTh2 antagonists-discovery of AZD1981," Bioorg. Med. Chem. Let., 2011, vol. 21, pp. 6288-6292.

Molinaro et al., "CRTH2 Antagonist MK-7246: A Synthetic Evolution from Discovery through Development," J. Org. Chem. 2012, vol. 77(5), pp. 2299-2309.

Pettipher et al., "Update on the Development of Antagonists of Chemoattractant Receptor-Homologous Molecule Expressed on Th2 Cells (CRTH2). From Lead Optimization to Clinical Proof-of-Concept in Asthma and Allergic Rhinitis," J. Med. Chem. 2012, vol. 55, pp. 2915-2931.

Pharmaceutical Salts and Co-crystals', Johan Wouters and Luc Quéré (Eds.), RSC Publishing, 2012 (10 pages).

Remington, The Science and Practice of Pharmacy, 21st Edition (2005), Part 5, "Pharmaceutical Manufacturing" published by Lippincott Williams & Wilkins (5 pages).

Robarge et al., "Isosteric ramatroban analogs: selective and potent CRTH-2 antagonists," Bioorg. Med. Chem Let. 2005, 15, 1749-1753.

Rosentreter et al., "Synthesis and Absolute Configuration of the New Thromboxane Antagonist (3R)-3-(4-Fluorophenylsulfonamido)-1,2,3,4-tetrahydro-9-carbazolepropanoic Acid and Comparison with its Enantiomer," Arzneim.-Forsch. 1989, vol. 39(12), pp. 1519-1521.

Royer et al., "A novel antagonist of prostaglandin D2 blocks the locomotion of eosinophils and basophils," Europ. J. Clin. Investigation 2008, vol. 38, pp. 663-671.

Sandham et al., "7-Azaindole-3-acetic acid derivatives: Potent and selective CRTh2 receptor antagonists," Bioorg. Med. Chem Let. 2009, vol. 19, pp. 4794-4798.

Sawyer et al., "Molecular pharmacology of the human prostaglandin D2 receptor, CRTH2," Br. J. Pharmacol, 2002, vol. 137, pp. 1163-1172.

Stearns et al., "Novel tricyclic antagonists of the prostaglandin D2 receptor DP2 with efficacy in a murine model of allergic rhinitis," Bioorg. Med. Chem. Lett. 2009, vol. 19, pp. 4647-4651.

Sugimoto et al., "An Orally Bioavailable Small Molecule Antagonist of CRTH2, Ramatroban (BAY u3405), inhibits Prostaglandin D2—Induced Eosinophil Migration in Vitro," Journal of Pharmacology and Experimental Therapeutics, vol. 305(1), pp. 347-352 (2003).

(56) References Cited

OTHER PUBLICATIONS

Tumey et al., "3-Indolyl sultams as selective CRTh2 antagonists," Bioorg. Med. Chem Let. 2010, vol. 20, pp. 3287-3290.

Ulven et al., "Minor Structural Modifications Convert the Dual TP/CRTH2 Antagonist Ramatroban into a Highly Selective and Potent CRTH2 Antagonist," J. Med. Chem., 2005, vol. 48(4), pp. 897-900.

Ulven et al., "Synthesis and in vitro evaluation of a selective antagonist and the corresponding radioligand for the prostaglandin D2 receptor CRTH2," Bioorg. Med. Chem Let. 2007, vol. 17, pp. 5924-5927.

Valdenaire et al., "Evolution of novel tricyclic CRTH2 receptor antagonists from a (E)-2-cyano-3-(1H-indol-3-yl)acrylamide scaffold," Bioorg. Med. Chem. Lett. 2013, vol. 23(4), pp. 944-948.

* cited by examiner

CRYSTALLINE FORMS

CROSS REFERENCE TO RELATED APPLICATIONS

This application is a 35 U.S.C. 371 National Phase of PCT Application No. PCT/EP2016/071637 filed Sep. 14, 2016, which claims benefit to PCT Application No. PCT/EP2015/071060 filed Sep. 15, 2015, the disclosure of which is hereby incorporated by reference in its entirety.

The invention relates to a novel crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid (hereinafter also referred to as "COMPOUND"), processes for the preparation thereof, pharmaceutical compositions comprising said crystalline forms, pharmaceutical compositions prepared from such crystalline forms, and their use as prostaglandin $D_2$ receptor ("DP receptor") modulators, most particularly as $CRTH_2$ receptor ("DP2 receptor") modulators, in the treatment of various prostaglandin-mediated diseases and disorders. In particular, the COMPOUND in crystalline form may be used alone or in pharmaceutical compositions for the treatment of both, chronic and acute allergic/immune diseases/disorders such as asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease, rheumatoid arthritis, and nasal polyposis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia, DRESS syndrome (Drug Rash with Eosinophilia and Systemic Symptoms), and Still's disease (systemic onset juvenile idyiopathic arthritis); basophil-related diseases, comprising basophilic leukemia and basophilic leucocytosis; and cystic fibrosis.

BACKGROUND OF THE INVENTION

As a response to allergen exposure in allergic conditions, mast cells are activated and release mediators like histamine, thromboxane A2 (TxA2), cysteinyl leukotrienes (CysLTs) and prostaglandin $D_2$ ($PGD_2$). These mediators interact with their respective receptors and cause physiological effects such as increased vascular permeability, edema, pruritus, nasal and pulmonary congestion, bronchoconstriction, and mucus secretion. An increased vascular permeability for example, allows excessive infiltration of eosinophilic and basophilic leukocytes into the tissue and thus amplifies the allergic response.

Current treatments of allergic diseases comprise agents that can block or otherwise interrupt such interactions, e.g. anti-histamines (histamine H1 receptor antagonists), leukotriene receptor antagonists, beta-adrenergic receptor agonists, and corticosteroids. Generally, treatments with anti-histamines and leukotriene antagonists are limited in efficacy, and long-term usage of corticosteroids is often associated with unwanted side effects.

$PGD_2$ is an agonist known to act on two G-protein-coupled receptors, the $PGD_2$ receptor DP1 and the recently identified CRTH2 (chemoattractant receptor-homologous molecule expressed on Th2 cells) receptor (also referred to as "DP2 receptor").

Elevated $PGD_2$ levels are considered to cause inflammation as observed in allergic diseases such as allergic rhinitis, allergic asthma, allergic conjunctivitis, atopic dermatitis and the like. Therefore, blocking the interaction of $PGD_2$ with its receptors is considered a useful therapeutic strategy for the treatment of such diseases.

GB 2388540 discloses the use of ramatroban ((3R)-3-(4-fluorobenzene-sulfonamido)-1,2,3,4-tetrahydrocarbazole-9-propionic acid), a TxA2 receptor (also referred to as "TP receptor") antagonist with additional antagonistic activity on CRTH2, for the prophylaxis and treatment of allergic diseases, such as asthma, allergic rhinitis or allergic conjunctivitis. In T. Ishizuka et al., *Cardiovascular Drug Rev.* 2004, 22(2), 71-90 effects of ramatroban on late-phase inflammation are described. Furthermore, oral bioavailability of ramatroban and its ability to inhibit prostaglandin $D_2$-induced eosinophil migration in vitro has been reported (*Journal of Pharmacology and Experimental Therapeutics*, 305(1), p. 347-352 (2003)).

Azaindole acetic acid derivatives with CRTH2 antagonistic activity have been disclosed in WO 2010/054113, WO 2010/054114 and B. A. Stearns et al., Bioorg. Med. Chem. Lett. 2009, 19, 4647-4651.

WO 2011/117798 and WO 2012/140612 disclose (3-heteroarylamino-1,2,3,4-tetrahydro-9H-carbazol-9-yl)-acetic acid and (7-heteroarylamino-6,7,8,9-tetrahydropyrido[1,2-a]indol-10-yl)acetic acid derivatives, respectively, which derivatives have CRTH2 antagonistic activity.

It has surprisingly been found that COMPOUND has significantly improved properties in an in-vitro cytotoxicity assay in primary cultured rat hepatocytes. It is thus expected that COMPOUND has an improved toxicity profile in-vivo.

It has now been found that certain crystalline forms of COMPOUND may under certain conditions be found. Said crystalline forms of COMPOUND are novel and may have advantageous properties in view of the potential use of COMPOUND as active pharmaceutical ingredient. Such advantages may include better flow properties; less hygroscopicity; better reproducibility in manufacturing (for example better filtration parameters, better reproducibility of formation, and/or better sedimentation); and/or defined morphology. Such crystalline forms of COMPOUND may be particularly suitable in a process of manufacturing certain pharmaceutical compositions.

In the X-ray diffraction diagrams of FIG. 1 to FIG. 4 the angle of refraction 2 theta (2θ) is plotted on the horizontal axis and the counts on the vertical axis.

For avoidance of any doubt, the above-listed peaks describe the experimental results of the X-ray powder diffraction shown in FIGS. 1 to 4. It is understood that, in contrast to the above peak list, only a selection of characteristic peaks is required to fully and unambiguously characterize the COMPOUND in the respective crystalline form of the present invention.

Figure 5:
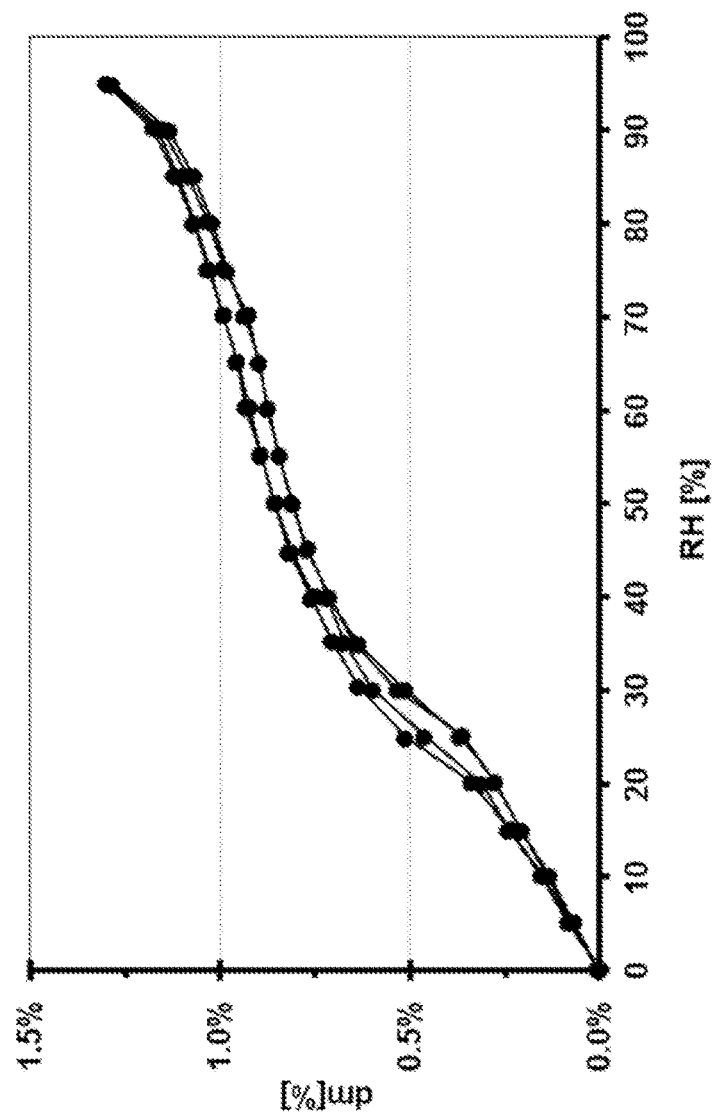

FIG. 5 shows the gravimetric vapour sorption diagram of COMPOUND in the crystalline form 1 as obtained from Example 1.

In the gravimetric vapour sorption diagram of FIG. 5 the relative humidity (% RH) is plotted on the horizontal axis and the mass change (% dm) on the vertical axis.

Figure 6:
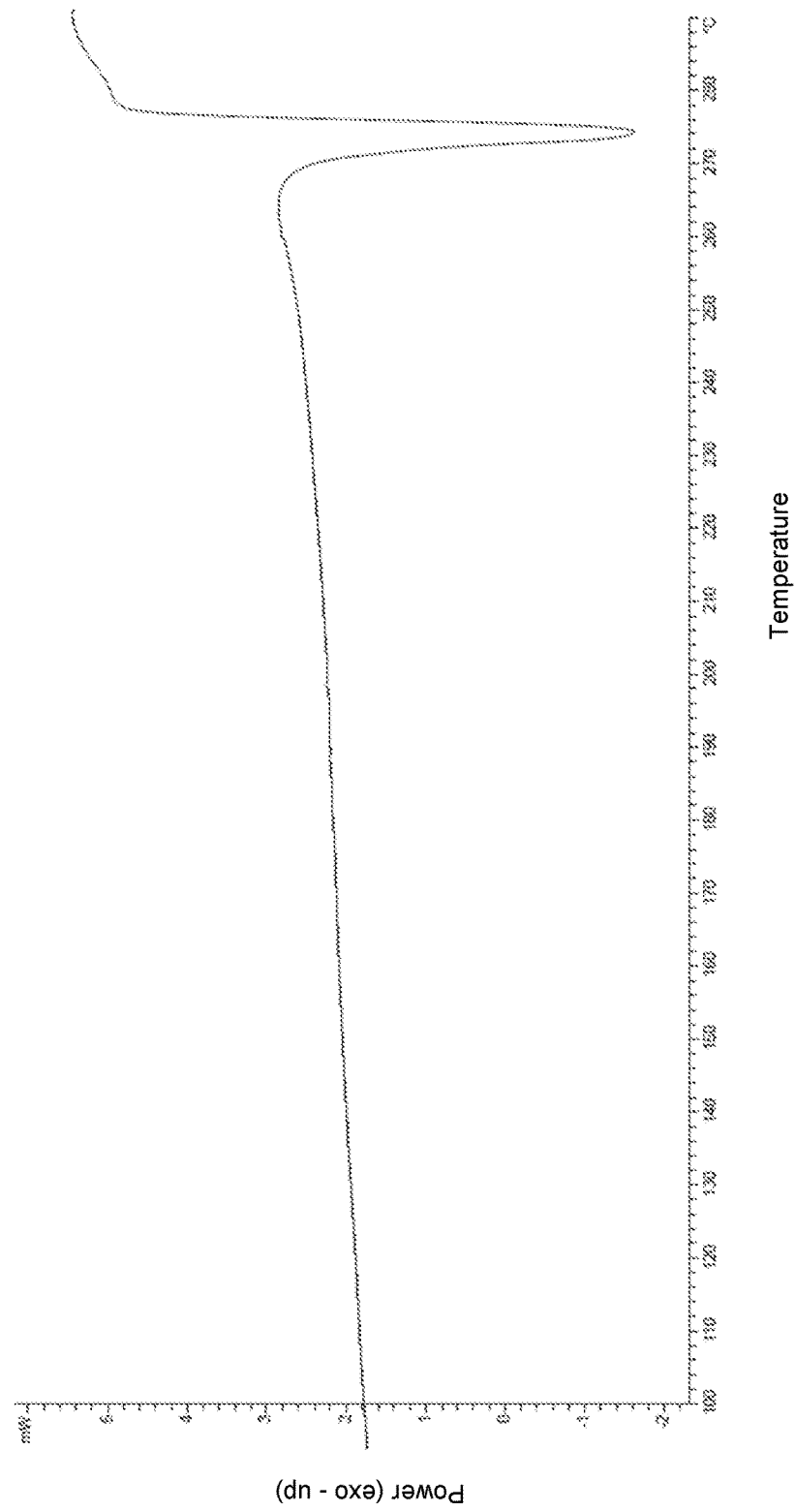

FIG. 6 shows the DSC trace of COMPOUND in the crystalline form 1.

In the DSC diagram of FIG. 6 the temperature (° C.) is plotted on the horizontal axis and the power (mW) on the vertical axis.

DETAILED DESCRIPTION OF THE INVENTION

1) A first embodiment of the invention relates to a crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid (COMPOUND); characterized by the presence of peaks in the X-ray powder diffraction diagram at the following angles of refraction 2θ: 12.6°, 14.0°, and 21.1°, wherein the X-ray powder diffraction diagram is measured at about 5%, at about 20%, at about 50%, or at about 95% relative humidity and at a temperature of about 25° C.

It is understood, that the crystalline form according to embodiment 1) comprise COMPOUND in a crystalline form of the free acid (i.e. not in form of a salt). Furthermore, said crystalline form may comprise non-coordinated and/or coordinated solvent (especially non-coordinated and/or coordinated water). Coordinated solvent (especially coordinated water) is used herein as term for a crystalline solvate (especially a crystalline hydrate). For the avoidance of doubt, in this application the term "crystalline hydrate" encompasses non-stoichiometric hydrates. Likewise, non-coordinated solvent is used herein as term for physiosorbed or physically entrapped solvent (definitions according to Polymorphism in the Pharmaceutical Industry (Ed. R. Hilfiker, VCH, 2006), Chapter 8: U. J. Griesser: The Importance of Solvates).

It is further understood, that the crystalline form may contain different amounts of coordinated water as a function of relative humidity and that the X-ray powder diffraction diagram may thus vary with relative humidity. For the avoidance of doubt, the present invention encompasses all crystalline sub-forms of the crystalline form that are reversibly converted into one another depending on relative humidity and that are characterized by the presence of the specifically given peaks in the X-ray powder diffraction diagram at a specifically given relative humidity and at about 25° C. It is understood that a reference to a measurement at a given relative humidity and at a given temperature means that the measurement is performed after the crystalline form has adapted to the specific relative humidity and temperature (i.e. after an equilibration time); typically the equilibration time is from about 0.5 h to about 24 h, notably from 1 h to 12 h and especially from 1 h to 6 h.

2) Another embodiment relates to a crystalline form of COMPOUND according to embodiment 1), characterized by:
   a. the presence of peaks in the X-ray powder diffraction diagram at the following angles of refraction 2θ: 12.6°, 14.0°, 19.8°, 20.0°, 21.1° and 26.4°, wherein the X-ray powder diffraction diagram is measured at about 5% relative humidity and at a temperature of about 25° C.; or
   b. the presence of peaks in the X-ray powder diffraction diagram at the following angles of refraction 2θ: 12.6°, 14.0°, 19.7°, 21.1° and 26.4°, wherein the X-ray powder diffraction diagram is measured at about 20% relative humidity and at a temperature of about 25° C.; or
   c. the presence of peaks in the X-ray powder diffraction diagram at the following angles of refraction 2θ: 12.6°, 14.0°, 19.5°, 21.1°, 21.4° and 26.1°, wherein the X-ray powder diffraction diagram is measured at about 50% relative humidity and at a temperature of about 25° C.; or
   d. the presence of peaks in the X-ray powder diffraction diagram at the following angles of refraction 2θ: 12.6°, 14.0°, 19.5°, 21.1°, 21.5° and 26.0°, wherein the X-ray powder diffraction diagram is measured at about 95% relative humidity and at a temperature of about 25° C.

3) Another embodiment relates to a crystalline form of COMPOUND according to embodiment 1), characterized by:
   a. the presence of peaks in the X-ray powder diffraction diagram at the following angles of refraction 2θ: 12.6°, 14.0°, 15.6°, 19.8°, 20.0°, 21.1°, 23.7°, 26.4°, 27.5° and 28.4°, wherein the X-ray powder diffraction diagram is measured at about 5% relative humidity and at a temperature of about 25° C.; or
b. the presence of peaks in the X-ray powder diffraction diagram at the following angles of refraction 2θ: 12.6°, 14.0°, 15.6°, 19.7°, 21.1°, 23.3°, 23.6°, 26.4°, 27.4°, and 28.4°, wherein the X-ray powder diffraction diagram is measured at about 20% relative humidity and at a temperature of about 25° C.; or
c. the presence of peaks in the X-ray powder diffraction diagram at the following angles of refraction 2θ: 12.6°, 14.0°, 15.2°, 16.1°, 19.5°, 21.1°, 21.4°, 23.0°, 26.1°, and 27.0°, wherein the X-ray powder diffraction diagram is measured at about 50% relative humidity and at a temperature of about 25° C.; or
d. the presence of peaks in the X-ray powder diffraction diagram at the following angles of refraction 2θ: 12.6°, 14.0°, 16.2°, 18.9°, 19.5°, 21.1°, 21.5°, 22.9°, 26.0°, and 27.0°, wherein the X-ray powder diffraction diagram is measured at about 95% relative humidity and at a temperature of about 25° C.

4) Another embodiment relates to a crystalline form of COMPOUND according to embodiment 1), characterized by the presence of peaks in the X-ray powder diffraction diagram at the following angles of refraction 2θ: 12.6°, 14.0°, and 21.1° (and notably 12.6°, 14.0°, 19.8°, 20.0°, 21.1° and 26.4°), wherein the X-ray powder diffraction diagram is measured at about 5% relative humidity and at a temperature of about 25° C.

5) Another embodiment relates to a crystalline form of COMPOUND according to embodiment 1), characterized by the presence of peaks in the X-ray powder diffraction diagram at the following angles of refraction 2θ: 12.6°, 14.0°, and 21.1° (and notably 12.6°, 14.0°, 19.7°, 21.1° and 26.4°), wherein the X-ray powder diffraction diagram is measured at about 20% relative humidity and at a temperature of about 25° C.

6) Another embodiment relates to a crystalline form of COMPOUND according to embodiment 1), characterized by the presence of peaks in the X-ray powder diffraction diagram at the following angles of refraction 2θ: 12.6°, 14.0°, and 21.1° (and notably 12.6°, 14.0°, 19.5°, 21.1°, 21.4° and 26.1°), wherein the X-ray powder diffraction diagram is measured at about 50% relative humidity and at a temperature of about 25° C.

7) Another embodiment relates to a crystalline form of COMPOUND according to embodiment 1), characterized by the presence of peaks in the X-ray powder diffraction diagram at the following angles of refraction 2θ: 12.6°, 14.0°, and 21.1° (and notably 12.6°, 14.0°, 19.5°, 21.1°, 21.5° and 26.0°), wherein the X-ray powder diffraction diagram is measured at about 95% relative humidity and at a temperature of about 25° C.

Figure 1:
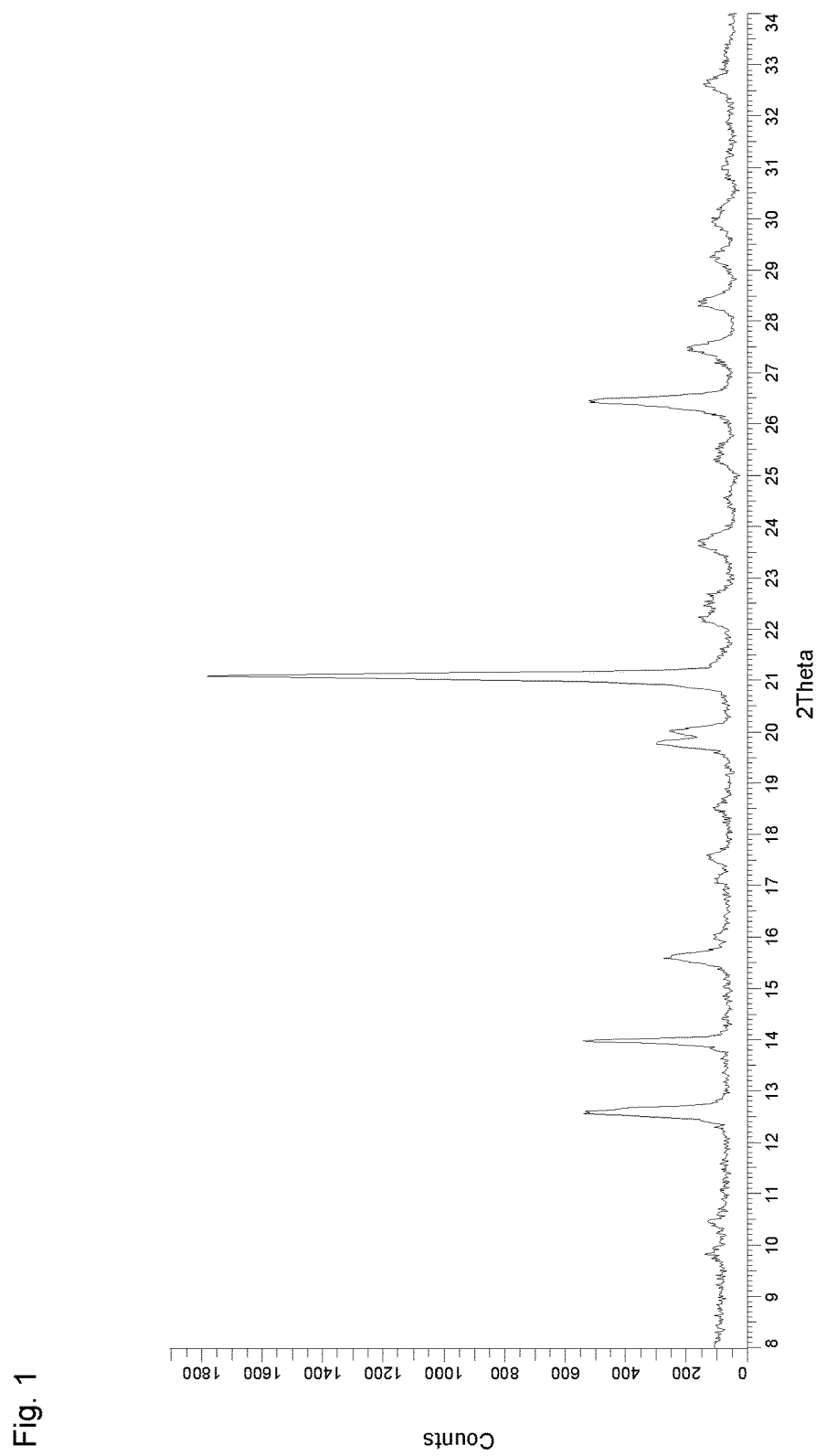
FIG. 1 shows the X-ray powder diffraction diagram of COMPOUND in the crystalline form 1 measured at 5% RH and 25° C., wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2 theta (selected peaks from the range 8-30° 2 theta with relative intensity larger than 10% are reported): 12.6° (27%), 14.0 (28%), 15.6° (11%), 19.8° (14%), 20.0° (11%), 21.1° (100%), and 26.4° (27%).
Figure 2:
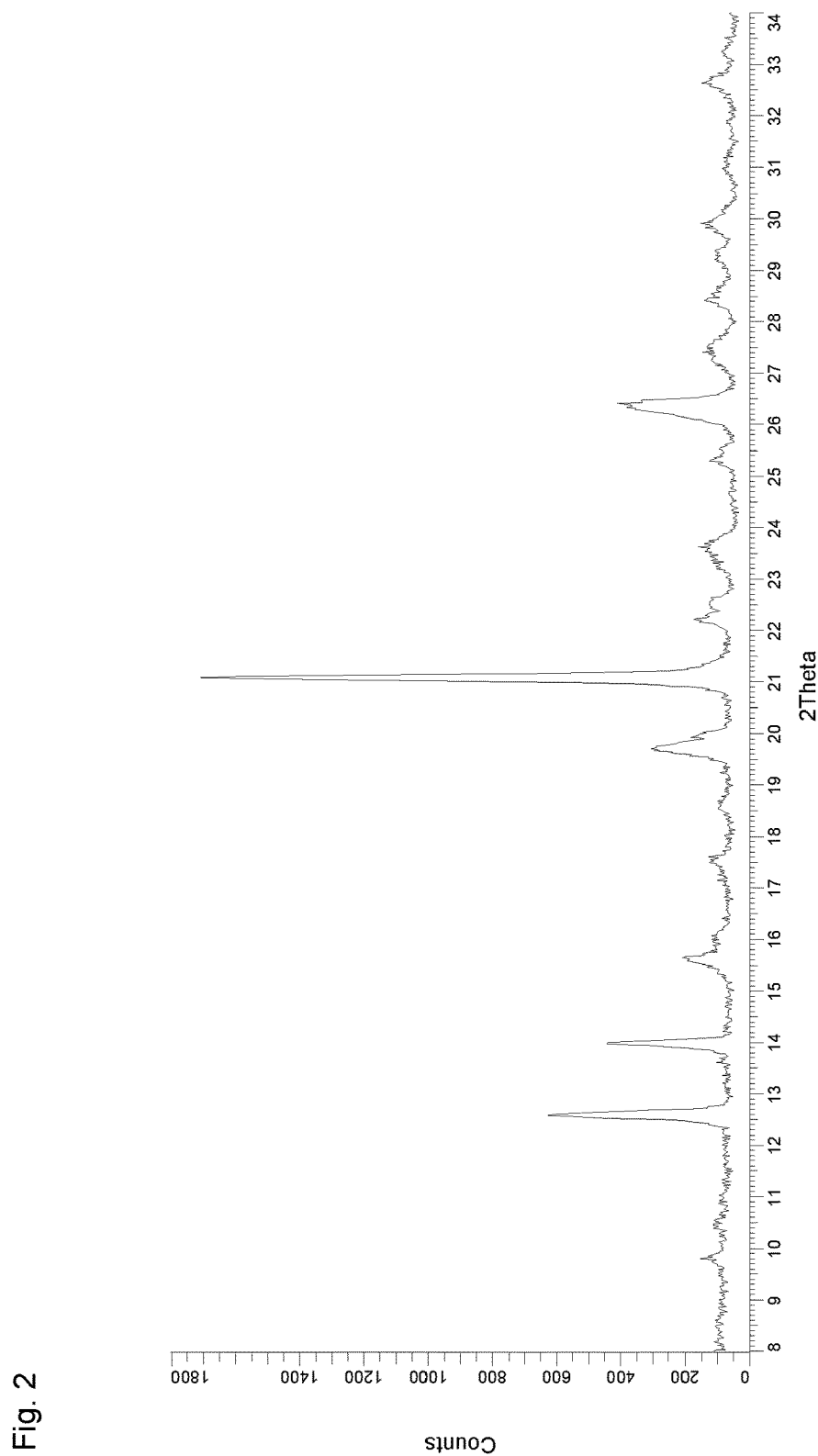
FIG. 2 shows the X-ray powder diffraction diagram of COMPOUND in the crystalline form 1 measured at 20% RH and 25° C., wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2 theta (selected peaks from the range 8-30° 2 theta with relative intensity larger than 10% are reported): 12.6° (34%), 14.0° (23%), 19.7° (14%), 21.1° (100%), and 26.4° (19%).
Figure 3:
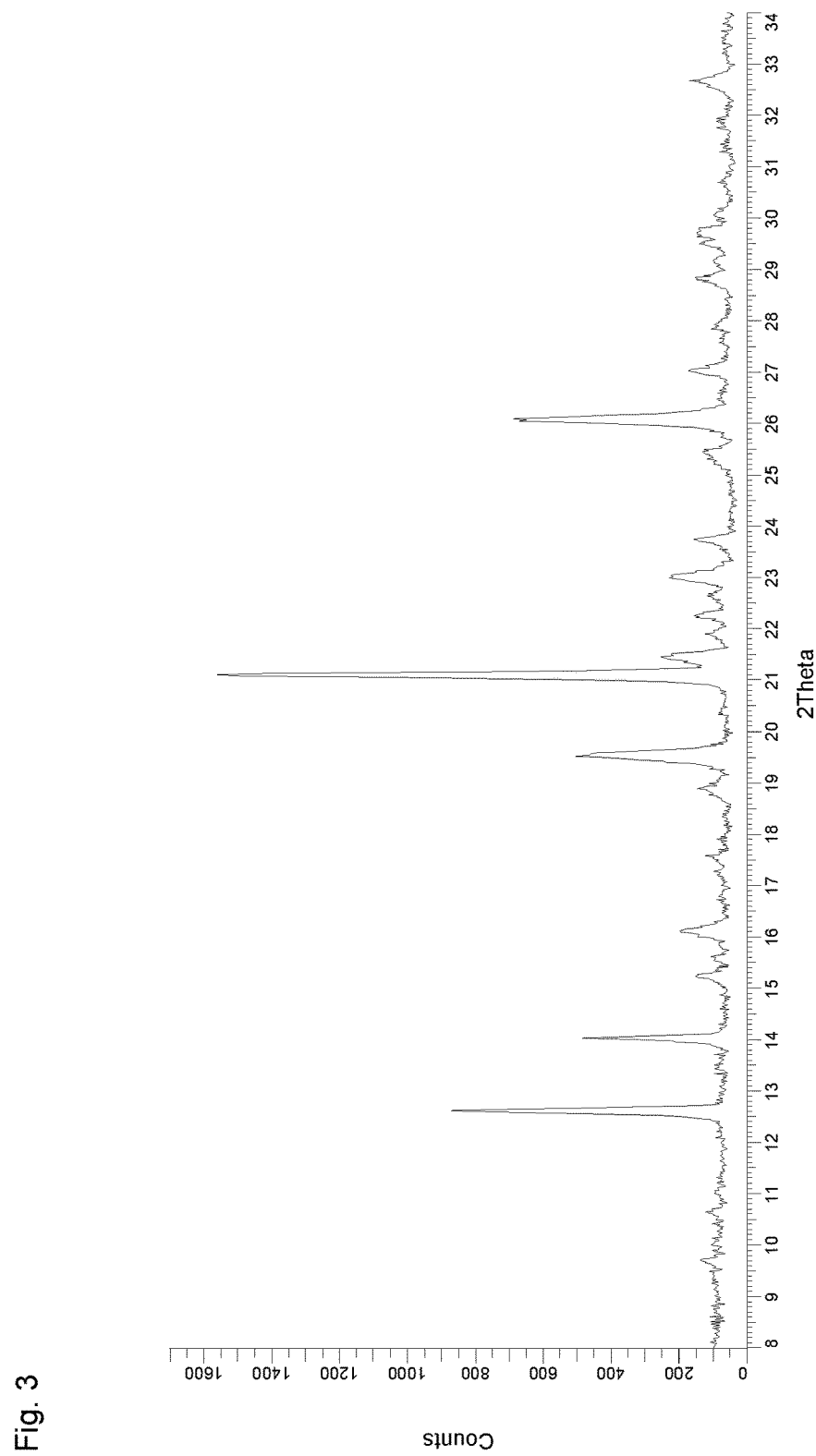
FIG. 3 shows the X-ray powder diffraction diagram of COMPOUND in the crystalline form 1 measured at 50% RH and 25° C., wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2 theta (selected peaks from the range 8-30° 2 theta with relative intensity larger than 10% are reported): 12.6° (54%), 14.0° (27%), 19.5° (30%), 21.1° (100%), 21.4° (12%), 23.0° (11%) and 26.1° (43%).
Figure 4:
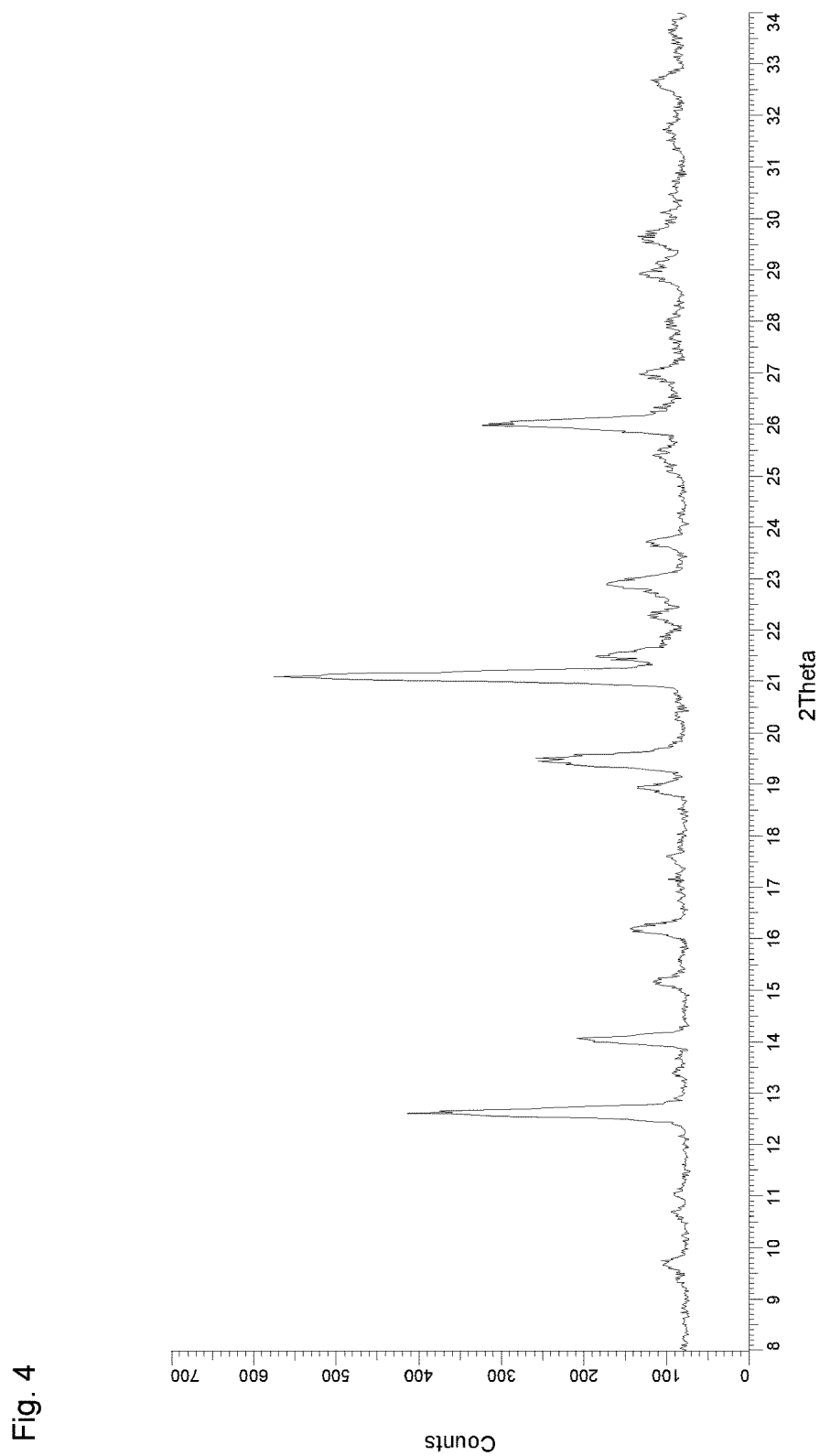
FIG. 4 shows the X-ray powder diffraction diagram of COMPOUND in the crystalline form 1 measured at 95% RH and 25° C., wherein the X-ray powder diffraction diagram is displayed against Cu Kα radiation. The X-ray diffraction diagram shows peaks having a relative intensity, as compared to the most intense peak in the diagram, of the following percentages (relative peak intensities given in parenthesis) at the indicated angles of refraction 2 theta (selected peaks from the range 8-30° 2 theta with relative intensity larger than 10% are reported): 12.6° (62%), 14.0° (24%), 16.2° (13%), 18.9° (11%), 19.5° (32%), 21.1° (100%), 21.5° (17%), 22.9° (18%) and 26.0° (47%).

8) Another embodiment relates to a crystalline form of COMPOUND according to embodiment 1),
  a. which essentially shows the X-ray powder diffraction pattern as depicted in FIG. 1, wherein the X-ray powder diffraction diagram is measured at about 5% relative humidity and at a temperature of about 25° C.; or
  b. which essentially shows the X-ray powder diffraction pattern as depicted in FIG. 2, wherein the X-ray powder diffraction diagram is measured at about 20% relative humidity and at a temperature of about 25° C.; or
  c. which essentially shows the X-ray powder diffraction pattern as depicted in FIG. 3, wherein the X-ray powder diffraction diagram is measured at about 50% relative humidity and at a temperature of about 25° C.; or
  d. which essentially shows the X-ray powder diffraction pattern as depicted in FIG. 4, wherein the X-ray powder diffraction diagram is measured at about 95% relative humidity and at a temperature of about 25° C.

9) Another embodiment relates to a crystalline form of COMPOUND according to embodiment 1), which essentially shows the X-ray powder diffraction pattern as depicted in FIG. 1, wherein the X-ray powder diffraction diagram is measured at about 5% relative humidity and at a temperature of about 25° C.

10) Another embodiment relates to a crystalline form of COMPOUND according to embodiment 1), which essentially shows the X-ray powder diffraction pattern as depicted in FIG. 2, wherein the X-ray powder diffraction diagram is measured at about 20% relative humidity and at a temperature of about 25° C.

11) Another embodiment relates to a crystalline form of COMPOUND according to embodiment 1), which essentially shows the X-ray powder diffraction pattern as depicted in FIG. 3, wherein the X-ray powder diffraction diagram is measured at about 50% relative humidity and at a temperature of about 25° C.

12) Another embodiment relates to a crystalline form of COMPOUND according to embodiment 1), which essentially shows the X-ray powder diffraction pattern as depicted in FIG. 4, wherein the X-ray powder diffraction diagram is measured at about 95% relative humidity and at a temperature of about 25° C.

13) Another embodiment relates to a crystalline form, such as an essentially pure crystalline form, of the compound (S)-2-(8-((5-chloropyrimidin-2-yl)(methyl)amino)-2-fluoro-6,7,8,9-tetrahydro-5H-pyrido[3,2-b]indol-5-yl)acetic acid obtainable by:
  a) preparation of a solution of COMPOUND in THF at 25 mg/mL;
  b) dispensing 0.2 mL of the solution in a 4 mL glass vial;
  c) evaporation of THF by use of an instrument that allows evaporation by combined use of infrared radiation, vortexing and vacuum set at 30° C. and 100 mbar for 30 minutes (e.g. a Combidancer from Hettich AG, Switzerland);
  d) addition of 0.02 mL of a solvent selected from ethylacetate, acetonitrile, acetone, or isopropanol (notably acetone) to the solid residue and allowing to incubate for 3 days at ambient temperature in the closed vial; and
  e) isolation of the obtained solid residue.

14) Another embodiment relates to a crystalline form of COMPOUND according to embodiment 13); characterized by the presence of peaks in the X-ray powder diffraction diagram at the following angles of refraction 2θ: 12.6°, 14.0°, and 21.1°, wherein the X-ray powder diffraction diagram is measured at about 5%, at about 20%, at about 50%, or at about 95% relative humidity and at a temperature of about 25° C.

15) Another embodiment relates to a crystalline form of COMPOUND according to embodiment 13), characterized by:
  a. the presence of peaks in the X-ray powder diffraction diagram at the following angles of refraction 2θ: 12.6°, 14.0°, 19.8°, 20.0°, 21.1° and 26.4°, wherein the X-ray powder diffraction diagram is measured at about 5% relative humidity and at a temperature of about 25° C.; or
  b. the presence of peaks in the X-ray powder diffraction diagram at the following angles of refraction 2θ: 12.6°, 14.0°, 19.7°, 21.1° and 26.4°, wherein the X-ray powder diffraction diagram is measured at about 20% relative humidity and at a temperature of about 25° C.; or c. the presence of peaks in the X-ray powder diffraction diagram at the following angles of refraction 2θ: 12.6°, 14.0°, 19.5°, 21.1°, 21.4° and 26.1°, wherein the X-ray powder diffraction diagram is measured at about 50% relative humidity and at a temperature of about 25° C.; or d. the presence of peaks in the X-ray powder diffraction diagram at the following angles of refraction 2θ: 12.6°, 14.0°, 19.5°, 21.1°, 21.5° and 26.0°, wherein the X-ray powder diffraction diagram is measured at about 95% relative humidity and at a temperature of about 25° C.

16) Another embodiment relates to a crystalline form of COMPOUND according to embodiment 13), characterized by:

a. the presence of peaks in the X-ray powder diffraction diagram at the following angles of refraction 2θ: 12.6°, 14.0°, 15.6°, 19.8°, 20.0°, 21.1°, 23.7°, 26.4°, 27.5° and 28.4°, wherein the X-ray powder diffraction diagram is measured at about 5% relative humidity and at a temperature of about 25° C.; or b. the presence of peaks in the X-ray powder diffraction diagram at the following angles of refraction 2θ: 12.6°, 14.0°, 15.6°, 19.7°, 21.1°, 23.3°, 23.6°, 26.4°, 27.4°, and 28.4°, wherein the X-ray powder diffraction diagram is measured at about 20% relative humidity and at a temperature of about 25° C.; or c. the presence of peaks in the X-ray powder diffraction diagram at the following angles of refraction 2θ: 12.6°, 14.0°, 15.2°, 16.1°, 19.5°, 21.1°, 21.4°, 23.0°, 26.1°, and 27.0°, wherein the X-ray powder diffraction diagram is measured at about 50% relative humidity and at a temperature of about 25° C.; or d. the presence of peaks in the X-ray powder diffraction diagram at the following angles of refraction 2θ: 12.6°, 14.0°, 16.2°, 18.9°, 19.5°, 21.1°, 21.5°, 22.9°, 26.0°, and 27.0°, wherein the X-ray powder diffraction diagram is measured at about 95% relative humidity and at a temperature of about 25° C.

17) Another embodiment relates to a crystalline form of COMPOUND according to embodiment 13), characterized by the presence of peaks in the X-ray powder diffraction diagram at the following angles of refraction 2θ: 12.6°, 14.0°, and 21.1° (and notably 12.6°, 14.0°, 19.8°, 20.0°, 21.1° and 26.4°), wherein the X-ray powder diffraction diagram is measured at about 5% relative humidity and at a temperature of about 25° C.

18) Another embodiment relates to a crystalline form of COMPOUND according to embodiment 13), characterized by the presence of peaks in the X-ray powder diffraction diagram at the following angles of refraction 2θ: 12.6°, 14.0°, and 21.1° (and notably 12.6°, 14.0°, 19.7°, 21.1° and 26.4°), wherein the X-ray powder diffraction diagram is measured at about 20% relative humidity and at a temperature of about 25° C.

19) Another embodiment relates to a crystalline form of COMPOUND according to embodiment 13), characterized by the presence of peaks in the X-ray powder diffraction diagram at the following angles of refraction 2θ: 12.6°, 14.0°, and 21.1° (and notably 12.6°, 14.0°, 19.5°, 21.1°, 21.4° and 26.1°), wherein the X-ray powder diffraction diagram is measured at about 50% relative humidity and at a temperature of about 25° C.

20) Another embodiment relates to a crystalline form of COMPOUND according to embodiment 13), characterized by the presence of peaks in the X-ray powder diffraction diagram at the following angles of refraction 2θ: 12.6°, 14.0°, and 21.1° (and notably 12.6°, 14.0°, 19.5°, 21.1°, 21.5° and 26.0°), wherein the X-ray powder diffraction diagram is measured at about 95% relative humidity and at a temperature of about 25° C.

21) Another embodiment relates to a crystalline form of COMPOUND according to embodiment 13), a. which essentially shows the X-ray powder diffraction pattern as depicted in FIG. 1, wherein the X-ray powder diffraction diagram is measured at about 5% relative humidity and at a temperature of about 25° C.; or b. which essentially shows the X-ray powder diffraction pattern as depicted in FIG. 2, wherein the X-ray powder diffraction diagram is measured at about 20% relative humidity and at a temperature of about 25° C.; or c. which essentially shows the X-ray powder diffraction pattern as depicted in FIG. 3, wherein the X-ray powder diffraction diagram is measured at about 50% relative humidity and at a temperature of about 25° C.; or d. which essentially shows the X-ray powder diffraction pattern as depicted in FIG. 4, wherein the X-ray powder diffraction diagram is measured at about 95% relative humidity and at a temperature of about 25° C.

22) Another embodiment relates to a crystalline form of COMPOUND according to embodiment 13), which essentially shows the X-ray powder diffraction pattern as depicted in FIG. 1, wherein the X-ray powder diffraction diagram is measured at about 5% relative humidity and at a temperature of about 25° C.

23) Another embodiment relates to a crystalline form of COMPOUND according to embodiment 13), which essentially shows the X-ray powder diffraction pattern as depicted in FIG. 2, wherein the X-ray powder diffraction diagram is measured at about 20% relative humidity and at a temperature of about 25° C.

24) Another embodiment relates to a crystalline form of COMPOUND according to embodiment 13), which essentially shows the X-ray powder diffraction pattern as depicted in FIG. 3, wherein the X-ray powder diffraction diagram is measured at about 50% relative humidity and at a temperature of about 25° C.

25) Another embodiment relates to a crystalline form of COMPOUND according to embodiment 13), which essentially shows the X-ray powder diffraction pattern as depicted in FIG. 4, wherein the X-ray powder diffraction diagram is measured at about 95% relative humidity and at a temperature of about 25° C.

26) Another embodiment relates to the crystalline form of COMPOUND according to any one of embodiments 1) to 25), which shows an endothermal event in the range of about 260° C. to 276° C. as determined by differential scanning calorimetry using the method as described herein.

27) Another embodiment relates to the crystalline form of COMPOUND according to any one of embodiments 1) to 26), which essentially shows a gravimetric moisture sorption profile as depicted in FIG. 5, wherein the gravimetric moisture sorption profile is measured at 25° C.

28) Another embodiment relates to the crystalline form of COMPOUND according to any one of embodiments 1) to 12), obtainable by the processes of embodiment 13).

Based on the dependencies of the different embodiments 1) to 28) as disclosed hereinabove, the following embodiments are thus possible and intended and herewith specifically disclosed in individualised form:

1, 2+1, 3+1, 4+1, 5+1, 6+1, 7+1, 8+1, 9+1, 10+1, 11+1, 12+1, 13, 14+13, 15+13, 16+13, 17+13, 18+13, 19+13,

20+13, 21+13, 22+13, 23+13, 24+13, 25+13, 26+1, 26+2+1, 26+3+1, 26+4+1, 26+5+1, 26+6+1, 26+7+1, 26+8+1, 26+9+1, 26+10+1, 26+11+1, 26+12+1, 26+13, 26+14+13, 26+15+13, 26+16+13, 26+17+13, 26+18+13, 26+19+13, 26+20+13, 26+21+13, 26+22+13, 26+23+13, 26+24+13, 26+25+13, 27+1, 27+2+1, 27+3+1, 27+4+1, 27+5+1, 27+6+1, 27+7+1, 27+8+1, 27+9+1, 27+10+1, 27+11+1, 27+12+1, 27+13, 27+14+13, 27+15+13, 27+16+13, 27+17+13, 27+18+13, 27+19+13, 27+20+13, 27+21+13, 27+22+13, 27+23+13, 27+24+13, 27+25+13, 27+26+1, 27+26+2, 27+26+3, 28+1, 28+2+1, 28+3+1, 28+4+1, 28+5+1, 28+6+1, 28+7+1, 28+8+1, 28+9+1, 28+10+1, 28+11+1, 28+12+1;

In the list above the numbers refer to the embodiments according to their numbering provided hereinabove whereas "+" indicates the dependency from another embodiment. The different individualised embodiments are separated by commas. In other words, "26+2+1" for example refers to embodiment 26) depending on embodiment 2), depending on embodiment 1), i.e. embodiment "26+2+1" corresponds to embodiment 1) further characterised by the features of the embodiments 2) and 26).

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2θ values as provided herein is in the range of +/−0.1-0.2°. Notably, when specifying an angle of refraction 2 theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

Where the plural form is used for compounds, solid, pharmaceutical compositions, diseases and the like, this is intended to mean also a single compound, solid, pharmaceutical composition, disease or the like.

Definitions provided herein are intended to apply uniformly to the subject matter as defined in any one of embodiments 1) to 28), and, mutatis mutandis, throughout the description and the claims unless an otherwise expressly set out definition provides a broader or narrower definition. It is well understood that a definition or preferred definition of a term or expression defines and may replace the respective term or expression independently of (and in combination with) any definition or preferred definition of any or all other terms or expressions as defined herein.

The term "enantiomerically enriched" is understood in the context of the present invention to mean especially that at least 90, preferably at least 95, and most preferably at least 99 percent by weight of the COMPOUND are present in form of one enantiomer of the COMPOUND. It is understood that COMPOUND is present in enantiomerically enriched absolute (S)-configuration.

The term "essentially pure" is understood in the context of the present invention to mean especially that at least 90, preferably at least 95, and most preferably at least 99 percent by weight of the crystals of COMPOUND are present in a crystalline form according to the present invention.

When defining the presence of peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 1, 2, 3 or 4, respectively, the term "essentially" means that at least the major peaks of the diagram depicted in said figures, i.e. those having a relative intensity of more than 20%, especially more than 10%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding relative humidity and temperatures, the term "about" placed before a numerical value "X" refers in the current application to an interval extending from X minus 10% of X to X plus 10% of X, and preferably to an interval extending from X minus 5% of X to X plus 5% of X. In the particular case of relative humidity, the term "about" placed before a relative humidity "Y" refers in the current application to an interval extending from relative humidity Y minus 3 of Y to Y plus 3 of Y, and preferably to an interval extending from Y minus 1 of Y to Y plus 1 of Y; for instance the term "about 5% relative humidity" refers to a relative humidity between 2% and 8%, and preferably to a relative humidity between 4% and 6%. In the particular case of temperatures, the term "about" placed before a temperature "Y" refers in the current application to an interval extending from the temperature Y minus 5° C. to Y plus 5° C., preferably to an interval extending from Y minus 3° C. to Y plus 3° C. Room temperature means a temperature of about 25° C.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or 1 to 4), this means that the variable is the integer 1, 2, 3, or 4.

The expression % w/w refers to a percentage by weight compared to the total weight of the composition considered. Likewise, the expression v/v refers to a ratio by volume of the two components considered.

The crystalline forms, especially the essentially pure crystalline forms, of COMPOUND according to any one of embodiments 1) to 28) can be used as medicaments, e.g. in the form of pharmaceutical compositions for enteral (such especially oral) or parenteral administration (including topical application or inhalation).

29) Another embodiment thus relates to a crystalline form of the compound (S)-2-(8-((5-chloropyrimidin-2-yl)(methyl)amino)-2-fluoro-6,7,8,9-tetrahydro-5H-pyrido[3,2-b]indol-5-yl)acetic acid according to any one of embodiments 1) to 28) for use as a medicament.

The crystalline solid, especially the essentially pure crystalline solid, of COMPOUND according to any one of embodiments 1) to 28) may be used as single component or as mixture with other crystalline forms or amorphous form of COMPOUND.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the crystalline form of the present invention, optionally in combination with other therapeutically valuable substances, into a galenical administration form together with suitable, non-toxic, inert, pharmaceutically acceptable solid or liquid carrier materials and, if desired, usual pharmaceutical adjuvants.

30) A further embodiment of the invention relates to pharmaceutical compositions comprising as active ingredient a crystalline form of COMPOUND according to any one of embodiments 1) to 28), and at least one pharmaceutically acceptable carrier material.

31) A further embodiment of the invention relates to a crystalline form of COMPOUND according to any one of embodiments 1) to 28), for use in the manufacture of a pharmaceutical composition, wherein said pharmaceutical composition comprises as active ingredient the COMPOUND, and at least one pharmaceutically acceptable carrier material.

32) A further embodiment of the invention relates to a crystalline form of COMPOUND according to any one of embodiments 1) to 28), for use in the prevention or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease, rheumatoid arthritis, and nasal polyposis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia, DRESS syndrome (Drug Rash with Eosinophilia and Systemic Symptoms), and Still's disease (systemic onset juvenile idyiopathic arthritis); basophil-related diseases, comprising basophilic leukemia and basophilic leucocytosis; and cystic fibrosis.

33) A preferred embodiment of the invention relates to a crystalline form of COMPOUND according to any one of embodiments 1) to 28), for use in the prevention or treatment of diseases selected from the group consisting of asthma, eosinophilic asthma, allergic rhinitis, atopic dermatitis, nasal polyposis, food allergy (notably IgE-mediated food allergy), urticaria (notably chronic urticaria), eosinophilic esophagitis, Churg Strauss Syndrome, hypereosinophilic syndrome, eosinophilic pneumonia (notably chronic eosinophilic pneumonia), DRESS syndrome, Still's disease, COPD and cystic fibrosis (and notably asthma, eosinophilic asthma, allergic rhinitis, atopic dermatitis, IgE-mediated food allergy, chronic urticaria, eosinophilic esophagitis and Churg Strauss Syndrome).

34) A further embodiment of the invention relates to a crystalline form of COMPOUND according to any one of embodiments 1) to 28), for use in the manufacture of a pharmaceutical composition for the prevention or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease, rheumatoid arthritis, and nasal polyposis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia, DRESS syndrome (Drug Rash with Eosinophilia and Systemic Symptoms), and Still's disease (systemic onset juvenile idyiopathic arthritis); basophil-related diseases, comprising basophilic leukemia and basophilic leucocytosis; and cystic fibrosis.

35) A preferred embodiment of the invention relates to a crystalline form of COMPOUND according to any one of embodiments 1) to 28), for use in the manufacture of a pharmaceutical composition for the prevention or treatment of diseases selected from the group consisting of asthma, eosinophilic asthma, allergic rhinitis, atopic dermatitis, nasal polyposis, food allergy (notably IgE-mediated food allergy), urticaria (notably chronic urticaria), eosinophilic esophagitis, Churg Strauss Syndrome, hypereosinophilic syndrome, eosinophilic pneumonia (notably chronic eosinophilic pneumonia), DRESS syndrome, Still's disease, COPD and cystic fibrosis (and notably asthma, eosinophilic asthma, allergic rhinitis, atopic dermatitis, IgE-mediated food allergy, chronic urticaria, eosinophilic esophagitis and Churg Strauss Syndrome).

36) A further embodiment of the invention relates to pharmaceutical compositions according to embodiment 30), for use in the prevention or treatment of diseases selected from the group consisting of chronic and acute allergic/immune diseases/disorders, comprising asthma, allergic asthma, eosinophilic asthma, severe asthma, rhinitis, allergic rhinitis, angioedema, insect venom allergy, drug allergies, allergic sinusitis, allergic nephritis, allergic conjunctivitis, atopic dermatitis, bronchial asthma, food allergy, systemic mast cell disorders, anaphylactic shock, urticaria, eczema, ulcerative colitis, chronic obstructive pulmonary disease (COPD), inflammatory bowel disease, rheumatoid arthritis, and nasal polyposis; eosinophil-related diseases comprising small vessel vasculitides like Churg-Strauss syndrome, Wegener's granulomatosis, microscopic polyangiitis (and organ-specific subsets of the latter), hypereosinophilic syndromes like eosinophilic pneumonia, eosinophilic esophagitis, reflux esophagitis, eosinophilic endocarditis (Loeffler's endocarditis), eosinophilia-myalgia syndrome, eosinophilic fasciitis, eosinophilic pustular folliculitis (Ofuji's disease), eosinophilic ulcers, angiolymphoid hyperplasia with eosinophilia (ALHE), eosinophilic cellulitis (Wells syndrome), chronic eosinophilic leukemia, DRESS syndrome (Drug Rash with Eosinophilia and Systemic Symptoms), and Still's disease (systemic onset juvenile idyiopathic arthritis); basophil-related diseases, comprising basophilic leukemia and basophilic leucocytosis; and cystic fibrosis.

37) A preferred embodiment of the invention relates to pharmaceutical compositions according to embodiment 30), for use in the prevention or treatment of diseases selected from the group consisting of asthma, eosinophilic asthma, allergic rhinitis, atopic dermatitis, nasal polyposis, food allergy (notably IgE-mediated food allergy), urticaria (notably chronic urticaria), eosinophilic esophagitis, Churg Strauss Syndrome, hypereosinophilic syndrome, eosinophilic pneumonia (notably chronic eosinophilic pneumonia), DRESS syndrome, Still's disease, COPD and cystic fibrosis (and notably asthma, eosinophilic asthma, allergic rhinitis, atopic dermatitis, IgE-mediated food allergy, chronic urticaria, eosinophilic esophagitis and Churg Strauss Syndrome).

The present invention also relates to a method for the prevention or treatment of a disease or disorder mentioned herein, comprising administering to a subject a pharmaceutically active amount of a crystalline form of COMPOUND according to any one of embodiments 1) to 28), or of a pharmaceutical composition according to embodiment 30).

The present invention also relates to a process for the preparation of COMPOUND in enantiomerically enriched form, and to processes for the preparation and characterization of the crystalline forms of COMPOUND according to any one of embodiments 1) to 28). Said processes are described in embodiment 13), as well as in the procedures of the experimental part below.

EXPERIMENTAL PROCEDURES

Abbreviations (as Used Hereinbefore or Hereinafter

Ac Acetyl (such as in OAc=acetate, AcOH=acetic acid)
aq. aqueous
Boc tert-Butoxycarbonyl
BSA Bovine serum albumine
Bu Butyl such as in n-Bu=n-butyl
conc. Concentrated
DCM Dichloromethane
DEA Diethylamine
DIEA Diisopropylethylamine
DMF N,N-Dimethylformamide
DMSO Dimethyl sulfoxide
dpm decays per minute
EDTA Ethylene Diamine Tetraacetic Acid
ELS(D) Evaporative Light-Scattering (Detection)
eq Equivalent(s)
Et Ethyl
EtOAc Ethyl acetate
EtOH Ethanol
FC Flash Chromatography on silica gel
Fig Figure
h Hour(s)
HEPES 4-(2-Hydroxyethyl)-piperazine-1-ethanesulfonic acid
$^1$H-NMR Nuclear magnetic resonance of the proton
HPLC High performance liquid chromatography
LC-MS Liquid chromatography-Mass Spectrometry
M Molarity
M Exact mass (as used for LC-MS)
Me Methyl
MeCN Acetonitrile
MeOH Methanol
MW Microwave
mW milli-Watt
μl microliter
min Minute(s)
MS Mass spectrometry
N Normality
PBS Phosphate Buffered Saline
Ph Phenyl
PPh$_3$ Triphenylphosphine
prep. Preparative
RH relative humidity
RT Room temperature
sat. Saturated
TFA trifluoroacetic acid
THF Tetrahydrofuran
$t_R$ Retention time
TRIS Tris-(hydroxymethyl)aminomethane buffer
UV Ultra violet All solvents and reagents are used as obtained from commercial sources unless otherwise indicated.

Temperatures are indicated in degrees Celsius (° C.). Unless otherwise indicated, the reactions take place at room temperature (RT).

In mixtures, relations of parts of solvent or eluent or reagent mixtures in liquid form are given as volume relations (v/v), unless indicated otherwise.

Compounds are purified by flash column chromatography on silica gel (FC) or by preparative HPLC. Compounds described in the invention are characterized by LC-MS (retention time $t_R$ is given in min.; molecular weight obtained from the mass spectrum is given in g/mol, using the conditions listed below).

Analytical LC-MS conditions as used in the Examples below:

LC-MS analyses are performed on a Agilent 1100 system, equipped with a Dionex P580 binary pump, a Dionex PDA-100 Photodiode Array Detector and a Finnigan AQA mass spectrometer.

The LC retention times are obtained using the following elution condition:

Analytical HPLC on a Zorbax® SB-AQ column (4.6×50 mm, 3.5 μm, Agilent); Linear gradient of water/0.04% TFA (A) and MeCN (B) from 5% to 95% B over 1.5 min; flow rate 4.5 ml/min, detection at 210 nm.

Preparative HPLC/MS purifications (basic conditions) are performed on a Gilson 333/334 binary high pressure gradient pump system with a Gilson 215 autosampler and fraction collector, a Dionex UVD340U DAD detector, a polymerlabs PL-ELS 1000 ELS detector and a Thermo MSQ Plus MS detector, using a Waters XBridge C18 column (10 μm, 30×75 mm), with a linear gradient of water/0.5% 25% NH$_4$OH (B) and MeCN (A) starting from 80/20 to 5/95 (B)/(A) over 5 min.; flow rate 75 ml/min.

Analytical HPLC over a chiral stationary phase are performed on a Daicel ChiralPak AD-H (4.6×250 mm, 5 μm) column or a Chiralpak AY-H (4.6×250 mm, 5 μm) column. Typical conditions of chiral HPLC are an isocratic mixture of 50% heptane+0.05% DEA and 50% EtOH+0.05% DEA, at a flow rate of 0.8 mL/min., detection at 210 nm (chiral HPLC-1) or an isocratic mixture of 40% heptane and 60% EtOH+0.1% TFA, at a flow rate of 1.0 mL/min., detection at 210 nm (chiral HPLC-2).

Preparative HPLC over a chiral stationary phase are performed on a Daicel ChiralPak AD-H (20×250 mm, 5 μm) column. Typical conditions of chiral HPLC are an isocratic mixture of 50% EtOH+0.05% DEA and 50% heptane, at a flow rate of 34 mL/min, detection at 210 nm.

X-Ray Powder Diffraction Analysis (XRPD)

X-ray powder diffraction patterns were collected on a Bruker D8 Advance X-ray diffractometer equipped with an Anton-Paar CHCplus+ chamber used to set and control temperature and relative humidity over the sample. The diffractometer was equipped with a Lynxeye detector, operated with CuKα-radiation with parallel beam optics and operated in reflection mode. Typically, the X-ray tube was run at of 40 kV/40 mA. A step size of 0.02° (2θ) and a step time of 95 sec over a scanning range of 3-35° in 2θ were applied. Powder was slightly pressed into a standard Anton-Paar TTK sample holder. Diffraction data are displayed using Cu Kα1 (λ=1.54060 Å). The accuracy of the 2θ values as provided herein is in the range of +/−0.1-0.2° as it is generally the case for conventionally recorded X-ray powder diffraction patterns.

Gravimetric Vapour Sorption (GVS) Analysis

Measurements were performed on a multi sample instrument SPS-100n (Projekt Messtechnik, Ulm, Germany) operated in stepping mode at 25° C. The sample was allowed to equilibrate at 40% RH before starting a pre-defined humidity program (40-0-95-0-95-40% RH, steps of 5% ΔRH and with a maximal equilibration time of 24 hours per step were applied. About 20 to 30 mg of each sample was used. The hygroscopic classification is done according to the European Pharmacopeia Technical Guide (1999, page 86), e.g., slightly hygroscopic: increase in mass is less than 2% and equal to or greater than 0.2% mass/mass; hygroscopic: increase in mass is less than 15% and equal to or greater than 2% mass/mass. The mass change between 20% relative humidity and 80% relative humidity in the first adsorption scan is considered.

Differential Scanning Calorimetry (DSC)

DSC data were collected on a Mettler Toledo STARe System (DSC822e module, measuring cell with ceramic sensor and STAR software version 13.00) equipped with a 34 position auto-sampler. The instrument was calibrated for energy and temperature using certified indium. Typically 2 mg of each sample, in an automatically pierced 40 μL Mettler aluminium pan, was heated at 10° C. min$^{-1}$, unless stated otherwise, from −20° C. to 320° C. A nitrogen purge at 20 ml min$^{-1}$ was maintained over the sample.

I—Chemistry

Synthesis of (S)-2-(8-((5-chloropyrimidin-2-yl)(methyl)amino)-2-fluoro-6,7,8,9-tetrahydro-5H-pyrido[3,2-b]indol-5-yl)acetic acid 1) Synthesis of 4-((5-chloropyrimidin-2-yl)(methyl)amino)cyclohexanone

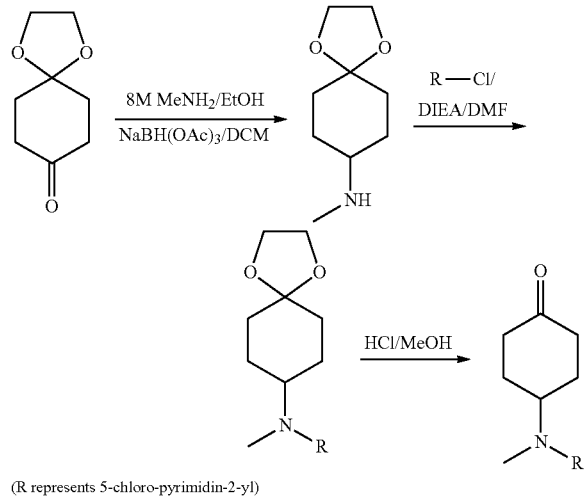

(R represents 5-chloro-pyrimidin-2-yl)

To a solution of commercially available 1,4-dioxaspiro[4.5]decan-8-one (1 eq) in DCM (20 ml/10 mmol) were added successively at 0° C. methyl amine (8M in EtOH, 1 eq) and NaBH(OAc)$_3$ (1.5 eq). The reaction mixture was allowed to warm to RT and stirred for 2 h. The reaction mixture was poured into a saturated solution of NaHCO$_3$, the organic layer was washed with brine, dried over MgSO$_4$ and evaporated in vacuo to give N-methyl-1,4-dioxaspiro[4.5]decan-8-amine which was used for the next step without further purification.

To a solution of N-methyl-1,4-dioxaspiro[4,5]decan-8-amine (1 eq) in DMF (10.5 ml/6 mmol) were added DIEA (2 eq) and 2,5-dichloropyrimidine (1.05 eq). The reaction mixture was stirred at 90° C. overnight. After cooling to RT, isopropyl acetate was added. The mixture was washed with water and 10% aq citric acid. The organic layer was dried (MgSO$_4$) and concentrated in vacuo. The crude product was purified by FC (0 to 15% EtOAc in heptane) to afford the desired intermediate compound as a solid.

A solution of this intermediate (1 eq) in a mixture of 2N HCl (2.7 ml/5 mmol) and MeOH (2.7 ml/5 mmol) was stirred at RT overnight. The aqueous layer was extracted with DCM. The organic layer was dried (MgSO$_4$) and concentrated in vacuo. The crude residue was purified by FC (0 to 17% EtOAc in heptane) to give the titled compound as a solid.

LC-MS: $t_R$=0.78 min; [M+H]$^+$=240.2

2.1) Synthesis of N-(5-chloropyrimidin-2-yl)-2-fluoro-N-methyl-6,7,8,9-tetrahydro-5H-pyrido[3,2-b]indol-8-amine (Method A)

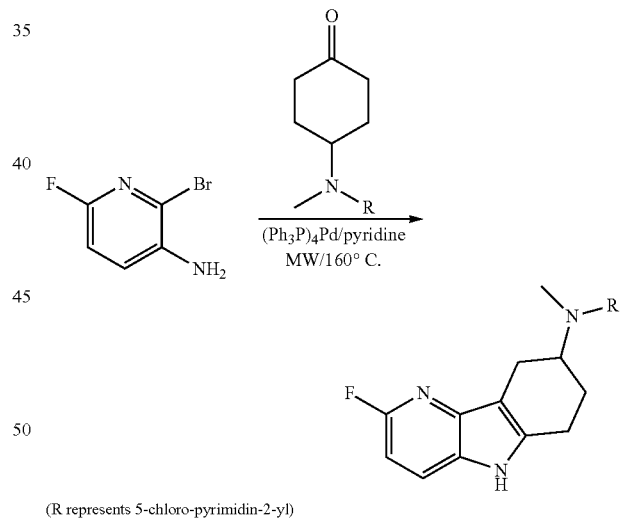

(R represents 5-chloro-pyrimidin-2-yl)

A solution of 3-amino-2-bromo-6-fluoro-pyridine (1 eq), 4-((5-chloropyrimidin-2-yl)(methyl)amino)cyclohexanone (1.2 eq), (Ph$_3$P)$_4$Pd (0.05 eq), and pyridine (8.17 eq) were combined in a vial. The vial was irradiated by MW at 160° C. for 1 h. (Ph$_3$P)$_4$Pd (0.025 eq) was added again and the reaction mixture was irradiated again by MW at 160° C. for 30 min. After cooling to RT, the reaction mixture was combined with water and extracted twice with DCM. The combined organic extracts were dried (MgSO$_4$), filtered and concentrated in vacuo. The residue was purified by prep. HPLC (basic conditions) to afford the desired product.

LC-MS: $t_R$=0.87 min; [M+H]$^+$=332.09.

2.2) Synthesis of N-(5-chloropyrimidin-2-yl)-2-fluoro-N-methyl-6,7,8,9-tetrahydro-5H-pyrido[3,2-b]indol-8-amine (Method B)

a) Synthesis of di-tert-butyl 1-(6-fluoropyridin-3-yl)hydrazine-1,2-dicarboxylate

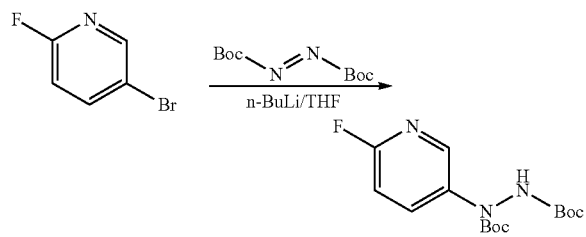

A solution of n-Butyllithium solution (1.6M in Hexane, 1.1 eq) was added dropwise at −40° C. to a solution of 5-bromo-2-fluoro-pyridine (1 eq) in diethylether (14.5 eq) under N₂ atmosphere. The reaction mixture was stirred for 20 min at −40° C. and then a solution of di-tert-butyl-azodicarboxylate (1.1 eq) in THF (18.5 eq) was added dropwise. The reaction mixture was stirred at −40° C. for 30 min and allowed to warm to RT over 30 min. Water was added followed by DCM. The organic phase was separated and dried over MgSO₄, filtered and concentrated in vacuo. The residue was purified by FC (EtOAc/n-heptane: 2/8) to afford the desired product.

LC-MS: $t_R$=0.88 min; [M+H]⁺=328.12.

b) Synthesis of N-(5-chloropyrimidin-2-yl)-2-fluoro-N-methyl-6,7,8,9-tetrahydro-5H-pyrido[3,2-b]indol-8-amine

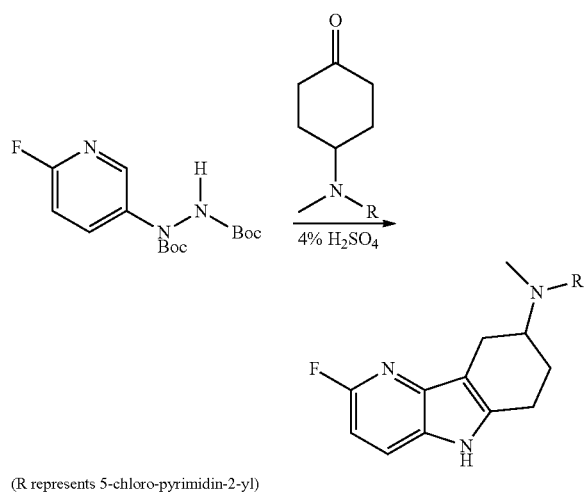

(R represents 5-chloro-pyrimidin-2-yl)

A solution of di-tert-butyl 1-(6-fluoropyridin-3-yl)hydrazine-1,2-dicarboxylate (1 eq), 4-((5-chloropyrimidin-2-yl)(methyl)amino)cyclohexanone (1 eq) in aqueous 4% H₂SO₄ (10 mL/0.04 mol) was stirred at 100° C. for 150 min. After cooling to RT, the reaction mixture was combined with sat. NaHCO₃ and extracted with EtOAc. The combined organic extracts were dried (MgSO₄), filtered and concentrated in vacuo. The residue was purified by prep. HPLC (basic conditions) to afford the desired product.

LC-MS: $t_R$=0.87 min; [M+H]⁺=332.03.

3) Synthesis of (S)-ethyl 2-(8-((5-chloropyrimidin-2-yl)(methyl)amino)-2-fluoro-6,7,8,9-tetrahydro-5H-pyrido[3,2-b]indol-5-yl)acetate and (R)-ethyl 2-(8-((5-chloropyrimidin-2-yl)(methyl)amino)-2-fluoro-6,7,8,9-tetrahydro-5H-pyrido[3,2-b]indol-5-yl)acetate

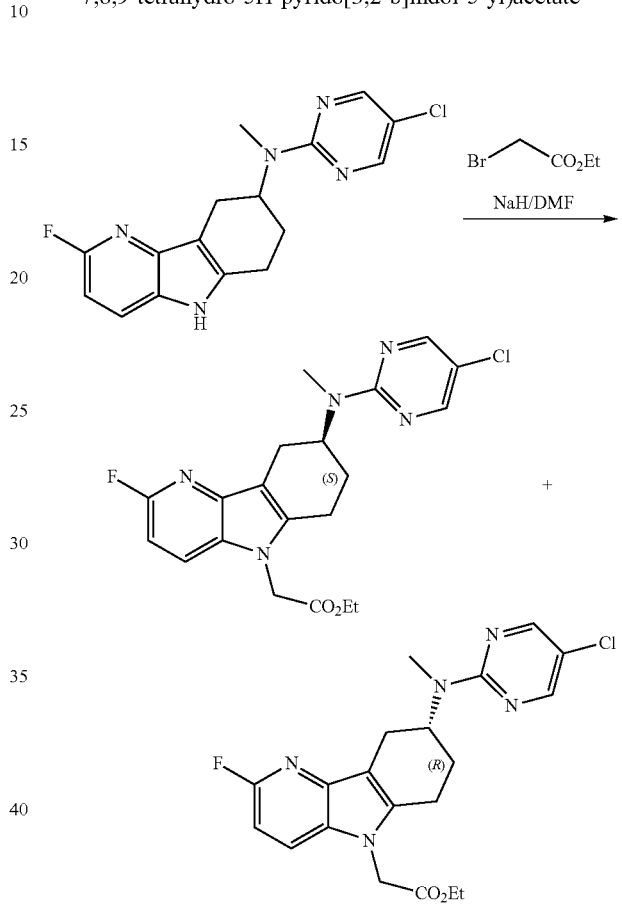

NaH (95%, 56.1 mg, 2.22 mmol, 1.2 eq) was added carefully to a cold solution (0° C.) of N-(5-chloropyrimidin-2-yl)-2-fluoro-N-methyl-6,7,8,9-tetrahydro-5H-pyrido[3,2-b]indol-8-amine (614 mg, 1.85 mmol, 1 eq) in DMF (6.36 mL). The reaction mixture was stirred for 20 min. Ethyl bromoacetate (0.23 mL, 2.04 mmol, 1.1 eq) was added slowly and the reaction mixture was allowed to warm to RT and stirred for 2 h. The reaction mixture was dissolved in EtOAc, and washed with a saturated solution of NaHCO₃. The organic extract was dried over MgSO₄, filtered and concentrated in vacuo. The residue was purified by FC (n-heptane to n-heptane/EtOAc: 7/3) to give the desired product as a racemate.

LC-MS: $t_R$: 0.96 min./[M+H]⁺: 418.01

The two enantiomers of the obtained product were separated by preparative HPLC over a chiral stationary phase:

(S)-ethyl 2-(8-((5-chloropyrimidin-2-yl)(methyl)amino)-2-fluoro-6,7,8,9-tetrahydro-5H-pyrido[3,2-b]indol-5-yl)acetate (271 mg, 35%): HPLC (chiral HPLC-1): $t_R$: 6.22 min;

(R)-ethyl 2-(8-((5-chloropyrimidin-2-yl)(methyl)amino)-2-fluoro-6,7,8,9-tetrahydro-5H-pyrido[3,2-b]indol-5-yl)acetate (273 mg, 35%): HPLC (chiral HPLC-1): $t_R$: 7.66 min.

4) Synthesis of (S)-2-(8-((5-chloropyrimidin-2-yl)(methyl)amino)-2-fluoro-6,7,8,9-tetrahydro-5H-pyrido[3,2-b]indol-5-yl)acetic acid

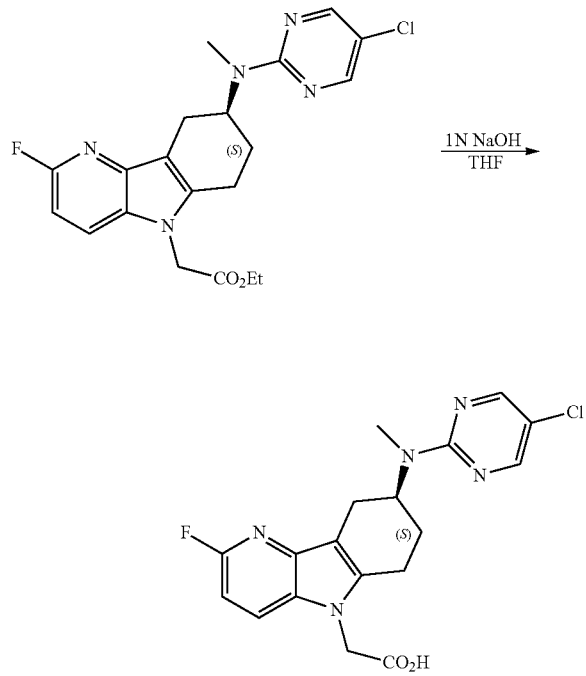

To a solution of (S)-ethyl 2-(8-((5-chloropyrimidin-2-yl)(methyl)amino)-2-fluoro-6,7,8,9-tetrahydro-5H-pyrido[3,2-b]indol-5-yl)acetate (271 mg, 0.649 mmol, 1 eq) in THF (10 mL) was added NaOH (1N, 10 mL, 10 mmol, 15.4 eq) at RT. The reaction mixture was stirred at RT for 1 h. The reaction mixture was concentrated in vacuo to remove only THF. It was then acidified with HCl conc. to pH~5-6 and stirred at RT. The suspension was extracted with EtOAc (4×). The combined organic layers were dried over $MgSO_4$, filtered and concentrated in vacuo to give the title compound as a beige solid (255 mg, 100%).

LC-MS: $t_R$: 0.82 min./[M+H]$^+$: 390.12
HPLC (chiral HPLC-2): $t_R$: 4.96 min.

II. Preparation of Crystalline Forms of Compound

Example 1: Preparation and Characterization of Compound in Crystalline Form 1

0.1 g of COMPOUND is dissolved in 4 mL THF and 0.2 mL of solution is given into a 4 mL brown glass vials. THF is evaporated from the vial by use of a Combidancer set at 30° C. and 100 mbar for 30 minutes (Hettich AG, Switzerland). A solid residue remains in the glass vial that is amorphous. 0.02 mL acetone is added to the solid residue, the vial is hermetically closed and the mixture is allowed to incubate for 3 days at ambient temperature in the closed vial. The solid residue is COMPOUND in crystalline form 1. Alternatively to acetone the procedure can be done using ethylacetate, acetonitrile, or isopropanol.

TABLE 1

Characterisation data for COMPOUND in crystalline form 1

| Technique | Data Summary | Remarks |
|---|---|---|
| XRPD | Crystalline | see FIGS. 1-4 |
| 1H-NMR | Consistent | |
| DSC | broad endothermal event below 100° C., due to evaporation of solvent. Further endothermic event in the range of about 260° C. to about 276° C. within an exothermic signal starting in a range of about 250° C. to about 260° C. and evolving beyond about 280° C. This is interpreted as concomitant melting/degradation event. The exact position of concomitant events of opposite sign is very dependent on the kinetics of the respective events and the person skilled in the art recognizes that statement of a precise melting point as peak temperature is not advisable in such instances. | see FIG. 6 |
| Hygroscopicity | Slightly hygroscopic (mass change larger then 0.2% and smaller then 2%) | See FIG. 5 |

III. Biological Assays

Preparation of hCRTH2 Receptor Membranes and Radioligand Displacement Assay:

First, recombinant HEK293-hCRTH$_2$ cells were detached from culture plates into 5 ml buffer A/plate (Buffer A: 5 mM Tris, 1 mM MgCl$_2$-6H$_2$O pH=7.4) using a rubber policeman. Cells were then transferred into centrifugation tubes and centrifuged for 5 min at 400 g. The cell pellet was resuspended in the same buffer and tubes were frozen at −80° C. Cells were thawed and membrane fragments were generated by homogenization using a polytron homogenizer (30 seconds). The membrane fragments were then centrifuged at 3000 g for 20 minutes and resuspended in buffer C (Buffer C: 75 mM Tris, 25 mM MgCl$_2$, 250 mM Saccharose pH 7.4). Aliquots of membrane fragements were stored at −20° C.

Binding assay was performed in a final assay volume of 250 µl First, 25 µl of test compound, previously diluted in Binding-Buffer (Binding-Buffer: 50 mM Tris-Base, 100 mM NaCl, 1 mM EDTA, 0.1% BSA (protease free), 0.01% NaN$_3$, 10 mM MnCl$_2$ pH 7.0) was placed into each well. After addition of 75 µl Binding-Buffer, 50 µl of the radioligand $^3$H-PGD$_2$ (at 2.5 nM (220.000 dpm/well) from ANAWA ART0662) was added to each well. Binding assay was started by addition of 100 µl CRTH$_2$ membrane fragments, reaching a final concentration of 20 µg/well. For non-specific binding, PGD$_2$ was added to the reaction mixture to 10 mM final concentration. This assay mix was incubated for 90 minutes at room temperature and then filtered through a GF/C filter 96-well plate which was pre-soaked for 3 hours in 0.5% polyethyleneimine (PEI). The filter-wells were washed three times with ice cold Binding-Buffer. Then, 40 µl of Microscint-40 (Packard) was added to each well and the retained radioactivity quantified in a Topcount (Packard).

Antagonistic activity of COMPOUND: IC$_{50}$=5.6 nM.

Radioligand Displacement Assay-Human Serum Albumin (HSA):

Radioligand displacement assay in presence of human serum albumin (HSA) was performed as described above, with following modifications. Binding-Buffer-HSA: Binding-buffer+0.5% Sigma Albumin from Human serum A1887 (instead of 0.1% BSA). A volume of 25 µl test compound, previously diluted in Binding-Buffer-HSA was placed into each well. After addition of 75 µl Binding-Buffer-HSA, 50 µl of $^3$H-PGD$_2$ (at 2.5 nM (220.000 dpm/well) from ANAWA ART0662) was added to each well. Remaining protocol was identical as described above.

Antagonistic activity of COMPOUND: IC$_{50}$=5.0 nM.

Eosinophil Shape Change Assay with Human Plasma

After obtaining informed consent, blood samples were drawn by venipuncture according to the protocol approved by the ethics committee of Basel, Switzerland. Polymorphonuclear leukocytes (containing eosinophils, basophils and neutrophils) were isolated using the Polymorphprep™ method (Axis-Shield). In brief, anticoagulated whole blood was layered onto a Polymorphprep gradient (density 1.113 g/ml) and centrifuged at 500 g for 30 min. The polymorphonuclear cell fraction was harvested and depleted for erythrocytes by hypotonic saline lysis.

The polymorphonuclear cells were resuspended in assay buffer (1×PBS with Ca$^{2+}$/Mg$^{2+}$ supplemented with 0.1% BSA, 10 mM HEPES, and 10 mM Glucose, pH 7.4) at 5×10$^6$ cells/ml and stained with anti-CD49d-APC ((APC=Allophycocyanin) for 1 hour at RT. Test compounds, at various concentrations, were preincubated 10 min in human plasma (anticoagulated with a thrombin inhibitor). Then, human plasma was added to the polymorphonuclear cells to 50% of final assay volume with polymorphonuclear cells at 4×10$^6$ cells/ml. After incubation for 10 minutes at 37° C., the polymorphonuclear cells were activated for 5 min at 37° C. by addition of PGD$_2$ at 100 nM final concentration. Activation was stopped by addition of 0.5 ml paraformaldehyde (1%).

Immediately after fixation with paraformaldehyde, the samples were analyzed by FACSCanto flow cytometer (BD Biosciences) and target cells were identified by their forward-scatter (FSC) and side-scatter (SSC) characteristics. Eosinophils were identified by the anti-CD49d-APC signal and their characteristic side-scatter (SSC) profile. Shape change responses, indicative of eosinophil activation, were quantified as the percent of cells with an increased forward-scatter.

Antagonistic activity of COMPOUND: IC$_{50}$=3.1 nM.

In Vitro Cytotoxicity in Primary Cultured Rat Hepatocytes

1. Methods 1.1 Isolation and Culture of Rat Hepatocytes

Adult male Wistar rats were narcotized with sodium pentobarbital and hepatocytes were isolated according to a standard procedure, i.e. by in situ perfusion of the liver with a collagenase solution. The viability of the purified hepatocytes, checked by the trypan blue dye exclusion method was greater than 85%. The isolated hepatocytes were resuspended in standard Williams Medium E, without phenol red, supplemented (WME supp.) with transferrin (100 µg/ml), triiodothyronine (10 µg/ml), gentamicin (50 µg/ml), hydrocortison hemisuccinate (13.36 µg/ml), glucagon (5 µg/ml), HEPES (10 mM), inosin (10 µg/ml), insulin (10 µg/ml), streptomycin (100 µg/ml) and penicillin (100 U/ml) and 10% fetal bovine serum (FBS). The cells were plated in collagen-coated 24-well plates at an initial density of 2×10$^5$ cells/well. After 4 h for attachment to the culture-plates, the medium was aspirated and replaced by fresh WME supp. without FBS containing the test compounds and incubated for 24 h at 37° C. in a 95% O$_2$ and 5% CO$_2$ atmosphere. For each experiment, i.e., with each batch of hepatocytes, treatments with the test compounds were done in quadruplicate. Quadriplicate controls (treatment with the vehicle only) were also present on each culture plate.

1.2 In Vitro Exposure to the Test Compounds

Stock solutions of the test compounds were prepared in DMSO a few hours before treatment start. Appropriate dilutions of these stock solutions were added to the culture media just prior to the treatment in order to give final concentrations of 0, 3, 10, 30, 100 and 300 µM. The final concentration of the vehicle DMSO was 1% (v/v).

1.3 Viability of the Cell Cultures 1.3.1 Monitoring of Monolayer Morphology

The morphology of the hepatocyte monolayers was monitored by light microscopy after 24 hours of exposure to the test compounds. Treatment related effects are described according to the following grading:

0 No morphological alterations observed upon treatment when compared to the control cultures 1-3 Treatment resulting in any morphological changes, e.g. intracellular granulation, vacuolization or cell death. Depending on the severity, these changes were regarded as slight (1), moderate (2) or strong (3).

K Treatment resulting in 100% dead cells and/or the complete detachment of the monolayer yielding a clear cell-free dish.

1.3.2 Leakage of Lactate Dehydrogenase

After 24 h treatment of the hepatocyte cultures, aliquots of culture medium were carefully collected and used for the analysis of lactate dehydrogenase (LDH) activity by spectrophotometry using the LDH cytotoxicity detection kit from Clontech (cat No. 630117, Mountain View, Calif., USA). For each experiment, additional cultures were used for the determination of total intracellular LDH activity at treatment start. For this purpose, 4 wells of cell culture per experiment were washed with cold saline before treatment start, sonicated in fresh medium and the homogenate was analyzed for total LDH activity. Enzyme activities in the culture media were assessed and expressed as percentage of the total activity present in the cultured hepatocytes at the beginning of the treatments.

2. Data Analysis

The lowest cytotoxic concentration (LCC) and the no effect concentration (NoEC) are given for each compound, based on cell morphology and LDH leakage after 24 h treatment. LCC is defined as the lowest concentration of the test compound leading to a clear effect on the cultured rat hepatocytes (morphology grading ≥2 or ≥2-fold increase in LDH leakage). A LCC value of >300 µM indicates the absence of effect on both endpoints at the highest test concentration of 300 µM. NoEC is defined as the highest test concentration of the compound which was without an effect on the cultured rat hepatocytes (morphology and LDH leakage).

3. Results: LCC and NoEC Values

| Compound | LCC [µM] | NoEC [µM] |
|---|---|---|
| COMPOUND | >300 | >300 |
| (example 9 from WO 2011/117798) | 300 | 30 |

In-Vivo Liver Toxicity:

Liver toxicity of a compound of formula (I) can be analyzed by oral treatment in rats and a non-rodent species of up to 4 weeks using three different doses of the compound. Reversibility of possible toxicity can be investigated in a subsequent treatment free period (recovery period). Dose levels are chosen based on dose range finding studies in the respective species. The high dose is expected to identify organ toxicity close at the maximum tolerated dose. The mid and low dose is chosen based on estimated therapeutic human exposures. Exposure of the compound is measured at each dose level.

At end of treatment and end of recovery liver biomarkers (such as for example liver enzymes, protein, triglycerides or cholesterol) are measured in the blood. In addition, Hematoxilin-Eosin stained liver slices is examined microscopically to directly assess possible organ damage. Specialized stainings of liver slices might be required to further characterize possible liver findings.

The invention claimed is:

1. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid, characterized by the presence of peaks in the X-ray powder diffraction diagram at the following angles of refraction 2: 12.6°, 14.0°, and 21.1°, wherein the X-ray powder diffraction diagram is measured at about 5%, at about 20%, at about 50%, or at about 95% relative humidity and at a temperature of about 25° C.

2. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1, characterized by:
   a. the presence of peaks in the X-ray powder diffraction diagram at the following angles of refraction 2: 12.6°, 14.0°, 19.8°, 20.0°, 21.1° and 26.4°, wherein the X-ray powder diffraction diagram is measured at about 5% relative humidity and at a temperature of about 25° C.; or
   b. the presence of peaks in the X-ray powder diffraction diagram at the following angles of refraction 2: 12.6°, 14.0°, 19.7°, 21.1° and 26.4°, wherein the X-ray powder diffraction diagram is measured at about 20% relative humidity and at a temperature of about 25° C.; or
   c. the presence of peaks in the X-ray powder diffraction diagram at the following angles of refraction 2: 12.6°, 14.0°, 19.5°, 21.1°, 21.4° and 26.1°, wherein the X-ray powder diffraction diagram is measured at about 50% relative humidity and at a temperature of about 25° C.; or
   d. the presence of peaks in the X-ray powder diffraction diagram at the following angles of refraction 2: 12.6°, 14.0°, 19.5°, 21.1°, 21.5° and 26.0°, wherein the X-ray powder diffraction diagram is measured at about 95% relative humidity and at a temperature of about 25° C.

3. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1, characterized by:
   a. the presence of peaks in the X-ray powder diffraction diagram at the following angles of refraction 2: 12.6°, 14.0°, 15.6°, 19.8°, 20.0°, 21.1°, 23.7°, 26.4°, 27.5° and 28.4°, wherein the X-ray powder diffraction diagram is measured at about 5% relative humidity and at a temperature of about 25° C.; or
   b. the presence of peaks in the X-ray powder diffraction diagram at the following angles of refraction 2: 12.6°, 14.0°, 15.6°, 19.7°, 21.1°, 23.3°, 23.6°, 26.4°, 27.4°, and 28.4°, wherein the X-ray powder diffraction diagram is measured at about 20% relative humidity and at a temperature of about 25° C.; or
   c. the presence of peaks in the X-ray powder diffraction diagram at the following angles of refraction 2: 12.6°, 14.0°, 15.2°, 16.1°, 19.5°, 21.1°, 21.4°, 23.0°, 26.1°, and 27.0°, wherein the X-ray powder diffraction diagram is measured at about 50% relative humidity and at a temperature of about 25° C.; or
   d. the presence of peaks in the X-ray powder diffraction diagram at the following angles of refraction 2: 12.6°, 14.0°, 16.2°, 18.9°, 19.5°, 21.1°, 21.5°, 22.9°, 26.0°, and 27.0°, wherein the X-ray powder diffraction diagram is measured at about 95% relative humidity and at a temperature of about 25° C.

4. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1,
   a. which essentially shows the X-ray powder diffraction pattern as depicted in FIG. 1, wherein the X-ray powder diffraction diagram is measured at about 5% relative humidity and at a temperature of about 25° C.; or
   b. which essentially shows the X-ray powder diffraction pattern as depicted in FIG. 2, wherein the X-ray powder diffraction diagram is measured at about 20% relative humidity and at a temperature of about 25° C.; or
   c. which essentially shows the X-ray powder diffraction pattern as depicted in FIG. 3, wherein the X-ray powder diffraction diagram is measured at about 50% relative humidity and at a temperature of about 25° C.; or
   d. which essentially shows the X-ray powder diffraction pattern as depicted in FIG. 4, wherein the X-ray powder diffraction diagram is measured at about 95% relative humidity and at a temperature of about 25° C.

5. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid obtainable by:
   a) preparation of a solution of (S)-2-(8-((5-chloropyrimidin-2-yl)(methyl)amino)-2-fluoro-6,7,8,9-tetrahydro-5H-pyrido[3,2-b]indol-5-yl)acetic acid in THF at 25 mg/mL;
   b) dispensing 0.2 mL of the solution in a 4 mL glass vial;
   c) evaporation of THF by use of an instrument that allows evaporation by combined use of infrared radiation, vortexing and vacuum set at 30° C. and 100 mbar for 30 minutes;
   d) addition of 0.02 mL of a solvent selected from ethylacetate, acetonitrile, acetone, or isopropanol to the solid residue and allowing to incubate for 3 days at ambient temperature in the closed vial; and
   e) isolation of the obtained solid residue.

6. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 5, characterized by the presence of peaks in the X-ray powder diffraction diagram at the following angles of refraction 2: 12.6°, 14.0°, and 21.1°, wherein the X-ray powder diffraction diagram is measured at about 5%, at about 20%, at about 50%, or at about 95% relative humidity and at a temperature of about 25° C.

7. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 5, characterized by:
   a. the presence of peaks in the X-ray powder diffraction diagram at the following angles of refraction 2: 12.6°, 14.0°, 19.8°, 20.0°, 21.1° and 26.4°, wherein the X-ray powder diffraction diagram is measured at about 5% relative humidity and at a temperature of about 25° C.; or
   b. the presence of peaks in the X-ray powder diffraction diagram at the following angles of refraction 2: 12.6°, 14.0°, 19.7°, 21.1° and 26.4°, wherein the X-ray powder diffraction diagram is measured at about 20% relative humidity and at a temperature of about 25° C.; or
   c. the presence of peaks in the X-ray powder diffraction diagram at the following angles of refraction 2: 12.6°, 14.0°, 19.5°, 21.1°, 21.4° and 26.1°, wherein the X-ray powder diffraction diagram is measured at about 50% relative humidity and at a temperature of about 25° C.; or
   d. the presence of peaks in the X-ray powder diffraction diagram at the following angles of refraction 2: 12.6°, 14.0°, 19.5°, 21.1°, 21.5° and 26.0°, wherein the X-ray powder diffraction diagram is measured at about 95% relative humidity and at a temperature of about 25° C.

8. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1, which shows an endothermal event in the range of about 260° C. to 276° C. as determined by differential scanning calorimetry.

9. A crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1, which essentially shows a gravimetric moisture sorption profile as depicted in FIG. 5, wherein the gravimetric moisture sorption profile is measured at 25° C.

10. A medicament comprising the crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1.

11. A pharmaceutical composition comprising as active ingredient a crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1, and at least one pharmaceutically acceptable carrier.

12. A method for treatment of a disease comprising administration of the crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 1, wherein the disease is nasal polyposis.

13. A method for treatment of a disease comprising administration of the crystalline form of (S)-2-(8-((5-chloropyrimidin-2-yl)(methyl)amino)-2-fluoro-6,7,8,9-tetrahydro-5H-pyrido[3,2-b]indol-5-yl)acetic acid according to claim 3, wherein the disease is nasal polyposis.

* * * * *

UNITED STATES PATENT AND TRADEMARK OFFICE
CERTIFICATE OF CORRECTION

PATENT NO. : 10,351,560 B2  
APPLICATION NO. : 15/759710  
DATED : July 16, 2019  
INVENTOR(S) : Hamed Aissaou et al.

Page 1 of 2

It is certified that error appears in the above-identified patent and that said Letters Patent is hereby corrected as shown below:

In the Specification

Under Column 9, paragraph 3, Line 24, "20" should read "2θ",

Under Column 9, paragraph 3, Line 27, "20" should read "2θ",

Under Column 9, paragraph 3, Line 32, "20+/-0.2°" should read "2θ+/-0.2°",

Under Column 9, paragraph 3, Line 34, "20+/-0.1°" should read "2θ+/-0.1°",

Under Column 15, paragraph 1, Line 5, "20" should read "2θ",

In the Claims

Under Column 23, Line 57, "2:" should read "2θ:",

Under Column 23, Line 66, "2:" should read "2θ:",

Under Column 24, Line 5, "2:" should read "2θ:",

Under Column 24, Line 11, "2:" should read "2θ:",

Under Column 24, Line 17, "2:" should read "2θ:",

Under Column 24, Line 26, "2:" should read "2θ:",

Under Column 24, Line 32, "2:" should read "2θ:",

Under Column 24, Line 38, "2:" should read "2θ:",

Signed and Sealed this  
Tenth Day of September, 2019

Andrei Iancu  
*Director of the United States Patent and Trademark Office*

CERTIFICATE OF CORRECTION (continued)
U.S. Pat. No. 10,351,560 B2

Under Column 24, Line 44, "2:" should read "2θ:",

Under Column 25, Claim 6, Line 23, "2:" should read "2θ:",

Under Column 25, Claim 7, Line 33, "2:" should read "2θ:",

Under Column 25, Claim 7, Line 38, "2:" should read "2θ:",

Under Column 26, Claim 7, Line 2, "2:" should read "2θ:",

Under Column 26, Claim 7, Line 8, "2:" should read "2θ:".